United States Patent
Svenstrup et al.

(10) Patent No.: US 9,643,970 B2
(45) Date of Patent: May 9, 2017

(54) SUBSTITUTED IMIDAZO [1,5-A]PYRAZINES AS PDE9 INHIBITORS

(71) Applicant: H Lundbeck A/S, Valby (DK)

(72) Inventors: Niels Svenstrup, Charlottenlund (DK); Klaus Baek Simonsen, Odense (DK); Lars Kyhn Rasmussen, Bronshoj (DK); Karsten Juhl, Greve (DK); Morten Langgard, Glostrup (DK); Kate Wen, Shanghai (CN); Yazhou Wang, Shanghai (CN)

(73) Assignee: H. Lundbeck A/S, Valby (DK)

( * ) Notice: Subject to any disclaimer, the term of this patent is extended or adjusted under 35 U.S.C. 154(b) by 63 days.

(21) Appl. No.: 14/434,308

(22) PCT Filed: Oct. 9, 2012

(86) PCT No.: PCT/EP2012/069936
§ 371 (c)(1),
(2) Date: Apr. 8, 2015

(87) PCT Pub. No.: WO2013/053690
PCT Pub. Date: Apr. 18, 2013

(65) Prior Publication Data
US 2015/0274736 A1    Oct. 1, 2015

(51) Int. Cl.
A61K 31/4985   (2006.01)
C07D 487/04   (2006.01)

(52) U.S. Cl.
CPC .................. C07D 487/04 (2013.01)

(58) Field of Classification Search
CPC .......................... A61K 31/4985; C07D 487/04
USPC ......................................... 514/249; 544/350
See application file for complete search history.

(56) References Cited

U.S. PATENT DOCUMENTS

| | | | |
|---|---|---|---|
| 6,362,178 | B1 | 3/2002 | Niewohner et al. |
| 7,709,468 | B2 | 5/2010 | Calderwood et al. |
| 8,299,080 | B2 | 10/2012 | Okada et al. |
| 8,563,565 | B2 | 10/2013 | Norimine et al. |
| 9,434,731 | B2 | 9/2016 | Siegel et al. |
| 2004/0220186 | A1 | 11/2004 | Bell et al. |
| 2012/0295925 | A1 | 11/2012 | Tung et al. |
| 2015/0045348 | A1 | 2/2015 | Svenstrup et al. |

FOREIGN PATENT DOCUMENTS

| | | |
|---|---|---|
| CA | 2296224 | 7/2000 |
| CN | 1344268 | 4/2002 |
| CN | 101448829 | 6/2009 |
| CN | 101557826 | 10/2009 |
| CN | 101687876 | 3/2010 |
| CN | 103313988 | 9/2013 |
| EP | 2123801 | 11/2009 |
| WO | WO 99/24433 | 5/1999 |
| WO | 03/037899 A1 | 5/2003 |
| WO | WO 03/037432 | 5/2003 |
| WO | WO 03/093270 | 11/2003 |
| WO | WO 2004/096811 | 11/2004 |
| WO | WO 2005/041972 | 5/2005 |
| WO | WO 2007/137819 | 12/2007 |
| WO | WO 2008/139293 | 11/2008 |
| WO | WO 2010/084438 | 7/2010 |
| WO | 2011028820 | 3/2011 |
| WO | 2012/040230 A1 | 3/2012 |
| WO | WO 2012/040230 | 3/2012 |
| WO | WO 2013/053690 | * 4/2013 |

OTHER PUBLICATIONS

Jordan, V. C. Nature Reviews: Drug Discovery, 2, 2003, 205.*
Chawla, et al. Current Research & Information on Pharmaceutical Sciences (CRIPS), 5(1), 2004, 9-12.*
Hackam, et al. JAMA, 296(14), 2006, 1731-1732.*
Berge, S.M. et al., (1977) "Pharmaceutical Salts," J. Pharma. Sci. 66:1-19.
Blokland, A. et al., (2006) "Improving Memory: A Role for Phosphodiesterases," Curr. Pharm. Des. 12(20):2511-2523.

(Continued)

*Primary Examiner* — Douglas M Willis

(74) *Attorney, Agent, or Firm* — DT Ward, PC; Donna T. Ward; Heng Zhu

(57) ABSTRACT

This invention is directed to compounds, which are PDE9 enzyme inhibitors. The invention provides a pharmaceutical composition comprising a therapeutically effective amount of a compound of the invention and a pharmaceutically acceptable carrier. The present invention also provides processes for the preparation of the compounds of formula (I)

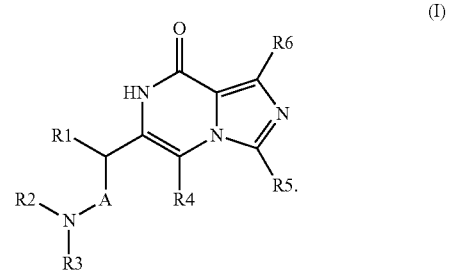

The present invention further provides a method of treating a subject suffering from a neurodegenerative disorder comprising administering to the subject a therapeutically effective amount of a compound of formula (I). The present invention further provides a method of treating a subject suffering from a psychiatric disorder comprising administering to the subject a therapeutically effective amount of a compound of formula (I).

10 Claims, No Drawings

(56) References Cited

OTHER PUBLICATIONS

Breer, H. et al., (1990) "Rapid Kinetics of Second Messenger Formation in Olfactory Transduction," Nature 345(6270):65-68.
Cooke, S.F. et al., (2006) "Plasticity in the Human Central Nervous System," Brain 129(7):1659-1673.
Duncton, M.A.J. et al., (2008) "Preparation of Aryloxetances and Arylazetidines by Use of an Alkyl-Aryl Suzuki Coupling," Organic Letters 10(15):3259-3262.
Fisher, D.A. et al., (1998) "Isolation and Characterization of PDE9A, a Novel Human cGMP-specific Phosphodiesterase," J. Biol. Chem. 273(25):15559-15564.
International Search Report and Written Opinion PCT/EP2012/069936 (WO 2013/053690) (2012) (9 pages).
International Search Report and Written Opinion PCT/EP2013/051451 (WO 2013/110768) (2013) (11 pages).
Mehats, C. et al., (2002) "Cyclic Nucleotide Phosphodiesterases and Their Role in Endocrine Cell Signaling," TRENDS in Endocrinol. & Metab. 13:29-35.
Van der Staay, J. F. et al., (2008) "The Novel Selective PDE9 Inhibitor BAY 73-6691 Improved Learning and Memory in Rodents," Neuropharma. 55(5):908-918.
Wunder, F. et al., (2005) "Characterization of the First Potent and Selective PDE9 Inhibitor Using a cGMP Reporter Cell Line," Mol. Pharmacol. 68(6):1775-1781.
Zhou, M. et al., (1994) "Role of Guanylyl Cyclase and cGMP-dependent Protein Kinase in Long-term Potentiation," Nature 368(6472):635-639.
The State Intellectual Property Office of the People's Republic of China Second Office Action dated Oct. 14, 2016 Application No. 201280076285.6, entitled PDE9I With Imidazo Pyrazinone Backbone and English Translation included.
Extended European Search Report dated Oct. 25, 2016 in Application No. 16185105.0, entitled PDE9I With Imidazo Pyrazinone Backbone.
Verhoest et al., 2009, "Identification of a Brain Penetrant PDE9A Inhibitor Utilizing Prospective Design and Chemical Enablement as a Rapid Lead Optimization Strategy", Journal of Medicinal Chemistry, vol. 52, No. 24, pp. 7946-7949.

* cited by examiner

SUBSTITUTED IMIDAZO [1,5-A]PYRAZINES AS PDE9 INHIBITORS

CROSS-REFERENCE TO RELATED APPLICATIONS

This is a national stage application of International Application No. PCT/EP2012/069936 filed Oct. 9, 2012.

FIELD OF THE INVENTION

The present invention relates to cyclic guanylate monophosphate (cGMP)-specific phosphodiesterase type 9 inhibitors (hereinafter referred to as PDE9 inhibitors) of the form 7H-imidazo[1,5-a]pyrazin-8-ones for the use as a medicament. Moreover the invention relates to a pharmaceutical composition comprising 7H-imidazo[1,5-a]pyrazin-8-ones, as well as a process for preparation of the compounds.

BACKGROUND OF THE INVENTION

The phosphodiesterases (PDEs) are a superfamily of enzymes that metabolically inactivate the ubiquitous intracellular messengers cAMP and cGMP. This function involves the PDEs in a broad range of important cellular functions, such as immune response, memory, and vision. The human genome encodes for 21 PDEs that are categorized into 11 families (Mehats C, Andersen C B, Filopanti M, Jin S L, Conti M. "Cyclic nucleotide phosphodiesterases and their role in endocrine cell signaling." Trends Endocrinol Metab. 2002; 13:29-35). These enzymes share a conserved catalytic domain of approximately 300 amino acids that is located in the C-terminal region of the protein. The N-terminal regions, which vary among different PDEs, serve regulatory functions including autoinhibition of the catalytic domains or control of subcellular localization (Mehats 2002). The PDEs have different substrate preferences: Cyclic guanylate monophosphate (cGMP)-specific phosphodiesterase type 9 (PDE9) is a member of the PDE enzyme family that selectively hydrolyses cGMP over cAMP (D A Fisher et al., J. Biol. Chemistry, vol. 273, No. 25, 15559-15564 (1998)). The different substrate preferences, combined with different expression profiles, cellular compartmentalization, and regulation, allow the PDEs to play a very versatile role in cell signal transduction (Breer H, Boekhoff I, Tareilus E. "Rapid kinetics of second messenger formation in olfactory transduction." Nature. 1990; 345:65-68).

PDE9 inhibitors have been reported as useful to treat cardiovascular disorders (WO 03/037899), and insulin resistance syndrome, hypertension, and/or type 2 diabetes (WO 03/037432) as well as for treatment of obesity related conditions (WO/2005/041972).

Wunder F. et al (Mol. Pharmacol. 2005 December; 68(6): 1775-81, 2005) report the in vitro characterization of 1-(2-chlorophenyl)-6-[(2R)-3,3,3-trifluoro-2-methylpropyl]-1,5-dihydro-4H-pyrazolo[3,4-d]pyrimidine-4-one, a selective inhibitor of phosphodiesterase 9 (PDE9), which is under development for the treatment of Alzheimer's disease. This compound is reported to inhibit human (IC50=55 nM) and murine (IC50=100 nM) PDE9 activity in vitro.

Over the years convincing experimental evidence has accumulated supporting the cognition-enhancing properties of several classes of PDE-inhibitors (Blokland et al., 2006: "Improving memory; a role for phosphordiesterases", Current Pharmacological Design 12, 2511-2523).

In a later study van der Staay et al. (F. Josef van der Staay, Neuropharmacology Volume 55, Issue 5, October 2008, pages 908-918) concludes that the PDE9 inhibitor 1-(2-chlorophenyl)-6-[(2R)-3,3,3-trifluoro-2-methylpropyl]-1,5-dihydro-4H-pyrazolo[3,4-d]pyrimidine-4-one may act as a putative cognition enhancer.

Alzheimers disease is the most common form of dementia, it is incurable, degenerative, and terminal. The typical symptoms are cognitive difficulties, difficulties with executive functioning (such as planning, organization, mental flexibility and task coordination) as well as with perception (agnosia) and execution of movements (apraxia).

Because AD cannot be cured and is degenerative, palliative treatment of patients is essential.

SUMMARY OF THE INVENTION

The present invention discloses novel PDE9 inhibitors for the use as a medicament, such as in the treatment of patients suffering from cognitive impairments, in particular cognitive impairments that relate to neurodegenerative diseases such as cortical dementia (e.g. Alzheimer's disease) or subcortical dementia, e.g. AIDS related dementia.

The PDE9 inhibitors of the present invention have the structure I (i.e. a 7H-imidazo[1,5-a]pyrazin-8-one backbone):

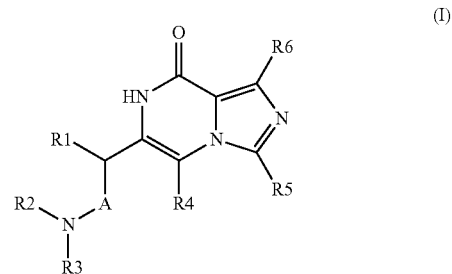

(I)

wherein R2 is cyclized with either R1 or R3.

The invention relates to methods of improving conditions involving PDE9, such as cognition, in particular the invention relates to a method of treating diseases involving cognitive difficulties, difficulties with executive functioning (such as planning, organization, mental flexibility and task coordination) as well as with pereception (agnosia). The methods of improving conditions involving PDE9 and/or treating diseases involving PDE9 comprises the administration of a compound of the present invention or a pharmaceutically acceptable salt, solvate or prodrug thereof to a patient in need thereof. The compound of the present invention or a pharmaceutically acceptable salt, solvate or prodrug thereof may be in the form of a pharmaceutical composition.

In a further aspect the invention relates to an improved pharmaceutical composition comprising a compound of the present invention particularly useful for the treatment of cognitive difficulties, difficulties with executive functioning (such as planning, organization, mental flexibility and task coordination) as well as with pereception (agnosia), in particular when associated neurodegenerative diseases, such as cortical or subcortical dementias, e.g. Alzheimer's disease (AD).

DETAILED DESCRIPTION OF THE INVENTION

Cognitive impairment includes a decline in cognitive functions or cognitive domains, such as, e.g., difficulties with attention, learning, memory and executive function (relevant reactions to external stimuli). Cognitive impairment also may include: deficits in attention, disorganized thinking, slow thinking, difficulty in understanding, poor concentration, impairment of problem solving, poor memory, difficulty in expressing thoughts and/or integrating thoughts, feelings and behaviour, and/or extinction of irrelevant thoughts, and difficulty in attention and vigilance, verbal learning and memory, visual learning and memory, speed of processing, social cognition, reasoning and problem solving, e.g., executive functioning. There are presently no effective drugs for the treatment of cognitive disorders on the market and there is a great need and demand for drugs effective in the treatment of such disorders.

Without being limited to any specific theory it is believed that the mode of action of PDE9 inhibitors can be understood in the light of the following neurological processes: guanylyl cyclase (alt. guanylate cyclase) converts guanosine triphosphate (GTP) to cyclic guanosine monophosphate (cGMP), which in turn activates cGMP-dependent protein kinase G (PKG). PKG is known to lower the threshold for the induction of long-term potentiation (LTP), i.e. the long-lasting improvement in communication between neurons (Zhou et al., 1994: "Role of guanylyl cyclase and cGMP-dependent protein kinase in long-term potentiation", Nature 368, 635-639). The communication between neurons takes place via the chemical synapses (synaptic transmission) and because memories are believed to be stored within these synapses, LTP is considered one of major cellular mechanisms that underlies cognition (Boron, W. F., 2005: Medical Physiology: A Cellular and Molecular Approach. Elsevier/Saunders, ISBN 1-4160-2328-3 and Cooke et al., 2006 "Plasticity in the human central nervous system". Brain 129, 1659-1673). As a result high levels of cGMP will eventually lead to improvement of cognition via the activation of PKG. The level of cGMP can be increased by inhibition of PDE9, which—as mentioned above—has the highest affinity for cGMP of any of the PDEs. Accordingly, PDE9 inhibitors will improve synaptic transmission and thereby enhance cognitive performance as evidenced by the results presented in the experimental section.

The invention will be illustrated in the following non-limiting examples.

EMBODIMENTS ACCORDING TO THE INVENTION

In a first embodiment (E1) the present invention relates to compounds having the structure (I) (also referred to as compounds of formula (I))

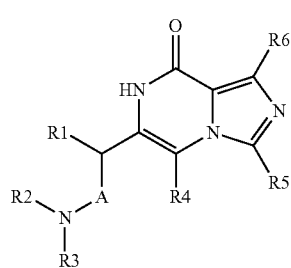

(I)

wherein R2 is cyclized with either R1 or R3, wherein R1, R2 and R3 are

R1, when cyclized with R2, is

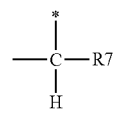

wherein R7 is selected from the group consisting of H, —CH$_3$, —C$_2$H$_5$, and —C$_3$H$_7$,
wherein * denotes the cyclization point, and
R1, when not cyclized, is selected from the group consisting of
H and

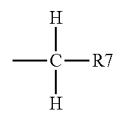

wherein R7 is selected from the group consisting of H, —CH$_3$, —C$_2$H$_5$, and —C$_3$H$_7$
R2 is a compound selected from the group consisting of

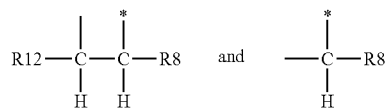

wherein R8 and R12 independently are selected from the group consisting of H, —CH$_3$, —C$_2$H$_5$, and —C$_3$H$_7$
wherein * denotes the cyclization point, and
R3, when cyclized with R2, is

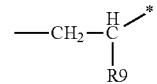

wherein * denotes the cyclization point, and
wherein R9 is selected from the group consisting of H, C$_1$-C$_6$ alkyl, branched C$_3$-C$_6$ alkyl, C$_3$-C$_6$ cycloalkyl, C$_6$-C$_{10}$ aryl, substituted C$_6$-C$_{10}$ aryl, C$_3$-C$_9$ heteroaryl, substituted C$_3$-C$_9$ heteroaryl, C$_1$-C$_6$ alkoxy, branched C$_3$-C$_6$ alkoxy, C$_3$-C$_6$ cycloalkoxy, C$_6$-C$_{10}$ aryloxy, substituted C$_6$-C$_{10}$ aryloxy, C$_3$-C$_9$ heteroaryloxy, substituted C$_3$-C$_9$ heteroaryloxy; and
R3, when not cyclized, is

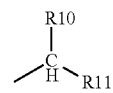

wherein
R10 is selected from the group consisting of H, —CH$_3$, and —C$_2$H$_5$; and
R11 is selected from the group consisting of C$_6$-C$_{10}$ aryl, substituted C$_6$-C$_{10}$ aryl, C$_3$-C$_9$ heteroaryl, substituted C$_3$-C$_9$ heteroaryl
R4 is selected from the group consisting of hydrogen, —CH$_3$, —C$_2$H$_5$, —C$_3$H$_7$, —CF$_3$, —CN, F and Cl;

R5 is selected from the group consisting of $C_6$-$C_{10}$ aryl, substituted $C_6$-$C_{10}$ aryl, $C_3$-$C_9$ heteroaryl, substituted $C_3$-$C_9$ heteroaryl, $C_3$-$C_6$ heterocyclyl, substituted $C_3$-$C_6$ heterocyclyl, $C_3$-$C_6$ cycloalkyl, and substituted $C_3$-$C_6$ cycloalkyl;

R6 is selected from the group consisting of hydrogen, F, Cl, CN, —$CH_3$, —$C_2H_5$, —$C_3H_7$, and —$CF_3$;

A is absent or —$CH_2$— and tautomers and pharmaceutically acceptable acid addition salts thereof, and polymorphic forms thereof.

In a further embodiment (E2) of (E1) the one or more heteroaryls of R5, R9 and R11 independently of each other comprise one or two nitrogen.

In a further embodiment (E3) of (E1) R9 is $C_1$-$C_3$ alkyl.

In a further embodiment (E4) of (E1) R9 is branched $C_1$-$C_3$ alkyl.

In a further embodiment (E5) of (E1) R9 is phenyl or napthyl.

In a further embodiment (E6) of (E1) R9 is substituted phenyl or substituted napthyl.

In a particular embodiment (E7) of any of embodiments (E1) and E(6) the substituent is selected from the group consisting of F, Cl, methyl, trifluoromethyl, methoxy, trifluoromethoxy, cyano, ethyl, dimethylamino, cyclopropyl, and isopropyl.

In a particular embodiment (E8) of (E7) the substituents are selected from the group consisting of F, Cl, methyl, trifluoromethyl, methoxy, trifluoromethoxy, cyano, ethyl, and dimethylamino.

In an embodiment (E9) of any of embodiments (E1) and (E2) R9 is a $C_4$-$C_9$ heteroaryl.

In a particular embodiment (E10) of embodiment (E9) R9 is selected from the group consisting of pyridyl, pyridazine, pyrimidinyl, pyrazinyl, quinolinyl, quinazolinyl, and quinoxalinyl.

In a further embodiment (E11) of any of embodiments (E1) and (E2) R9 is a substituted $C_4$-$C_9$ heteroaryl.

In a particular embodiment (E12) of embodiment (E11) R9 is selected from the group consisting of substituted pyridyl, substituted pyridazine, substituted pyrimidinyl, substituted pyrazinyl, substituted quinolinyl, and substituted quinazolinyl, and substituted quinoxalinyl.

In a particular embodiment (E13) of embodiment (E10) R9 is selected from the group consisting of 2-pyridyl, 3-pyridyl, 2-pyridazine, 2-pyrimidinyl, 4-pyrimidinyl, 2-pyrazinyl, 2-quinolinyl, 2-quinoxalinyl, 6-quinoxalinyl, and 2-quinazolinyl.

In a particular embodiment (E14) embodiment (E12) R9 is selected from the group consisting of substituted 2-pyridyl, substituted 3-pyridyl, substituted 2-pyridazine, substituted 2-pyrimidinyl, substituted 4-pyrimidinyl, substituted 2-pyrazinyl, substituted 2-quinolinyl, substituted 2-quinoxalinyl, substituted 6-quinoxalinyl, and substituted 2-quinazolinyl.

In a particular embodiment (E15) of any of embodiments (E1), (E2), (E11), (E12) and (E14) the substituent of R9 is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E16) of embodiment (E1) R9 is $C_1$-$C_4$ alkoxy.

In a particular embodiment (E17) of (E16) R9 is methoxy or ethoxy.

In an embodiment (E18) of embodiment (E1) R9 is branched $C_3$-$C_4$ alkoxy.

In a particular embodiment (E19) of (E18) R9 is isopropoxy or isobutoxy. In an embodiment (E20) of (E1), when R9 is $C_6$-$C_{10}$ aryloxy, R9 is selected from the group consisting of phenyloxy and naphtyloxy.

In an embodiment (E21) of (E1), when R9 is substituted $C_6$-$C_{10}$ aryloxy, R9 is selected from the group consisting of substituted phenyloxy and substituted naphtyloxy.

In a particular embodiment (E22) of any of embodiments (E1) and (E21) the substituents of R9, when R9 is a substituted $C_6$-$C_{10}$ aryloxy, is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E23) of any of embodiments (E1) and (E2) R9 is a $C_4$-$C_9$ heteroaryloxy.

In an embodiment (E24) of embodiment (E23) R9 is selected from the group consisting of pyridineoxy, pyridazineoxy, pyrimidineoxy and quinoxalineoxy.

In an embodiment (E25) of any of embodiments (E1) and (E2) R9 is a substituted $C_4$-$C_9$ heteroaryloxy.

In an embodiment (E26) of embodiment (E25) R9 is selected from the group consisting of substituted pyridineoxy, pyridazineoxy, substituted pyrimidineoxy and quinoxalineoxy In an embodiment (E27) of any of embodiments (E1), (E2), (E25) and (E26) the substituent is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E28) of embodiment (E1) R11 is a $C_6$-$C_{10}$ aryl selected from the group consisting of phenyl and naphthyl.

In a preferred embodiment (E29) of embodiment (E28) R11 is phenyl. In an embodiment (E30) of embodiment (E1) R11 is a substituted $C_6$-$C_{10}$ aryl selected from the group consisting of substituted phenyl and substituted naphthyl.

In a preferred embodiment (E31) of embodiment (E28) R11 is substituted phenyl.

In an embodiment (E32) of any of embodiments (E1), E(30) and E(31) the substituent is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E33) of any of embodiments (E1) and (E2) R11 is a $C_4$-$C_9$ heteroaryl.

In a particular embodiment (E34) of embodiment (E33) R11 is selected from the group consisting of pyridyl, pyridazine, pyrimidinyl, pyrazinyl, quinolinyl, quinazolinyl, and quinoxalinyl.

In a particular embodiment (E35) of embodiment (E34) R11 is selected from the group consisting of 2-pyridyl, 3-pyridyl, 2-pyridazine, 2-pyrimidinyl, 4-pyrimidinyl, 2-pyrazinyl, 2-quinolinyl, 2-quinoxalinyl, 6-quinoxalinyl, and 2-quinazolinyl.

In a further embodiment (E36) of any of embodiments (E1) and (E2) R11 is a substituted $C_4$-$C_9$ heteroaryl.

In a particular embodiment (E37) of embodiment (E36) R11 is selected from the group consisting of substituted pyridyl, substituted pyridazine, substituted pyrimidinyl, substituted pyrazinyl, substituted quinolinyl, and substituted quinazolinyl, and substituted quinoxalinyl.

In a particular embodiment (E38) of embodiment (E37) R11 is selected from the group consisting of substituted 2-pyridyl, substituted 3-pyridyl, substituted 2-pyridazine, substituted 2-pyrimidinyl, substituted 4-pyrimidinyl, substituted 2-pyrazinyl, substituted 2-quinolinyl, substituted 2-quinoxalinyl, substituted 6-quinoxalinyl, and substituted 2-quinazolinyl.

In a particular embodiment (E39) of any of embodiments (E1), (E2), (E36), (E37) and (E38) the substituent of R11 is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E40) of embodiment of embodiment (E1) R5 is selected from the group consisting of phenyl and naphthyl.

In an embodiment (E41) of embodiment (E1) R5 is substituted phenyl.

In an embodiment (E42) of embodiment (E41) the substituent is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E43) of embodiment of embodiment (E1) R5 is pyridyl.

In an embodiment (E44) of embodiment (E1) R5 is substituted pyridyl.

In an embodiment (E45) of embodiment (E44) the substituent is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E46) of embodiment (E1) R5 is selected from the group consisting of tetrahydropyranyl, tetrahydrofuranyl and piperidyl.

In an embodiment (E47) of embodiment (E1) R5 is selected from the group consisting of substituted tetrahydropyranyl, substituted tetrahydrofuranyl and substituted piperidyl.

In a particular embodiment (E48) of embodiment E(47) the substituent is selected from group consisting of F, Cl, methyl, cyano and methoxy.

In an embodiment (E49) of embodiment (E1) R5 is selected from the group consisting of cyclobutyl, cyclopentyl and cyclohexyl.

In a preferred embodiment (E50) of embodiment (E49) R5 is cyclopentyl or cyclohexyl.

In an embodiment (E51) of embodiment (E1) R5 is selected from the group consisting of substituted cyclobutyl, substituted cyclopentyl and substituted cyclohexyl.

In a preferred embodiment (E52) of embodiment (E51) R5 is substituted cyclopentyl or substituted cyclohexyl.

In an embodiment (E53) of any of embodiments (E51) and (E52) substituent is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E54) of embodiment (E1), the compound of formula (I) is selected among the compounds listed in Table 1, in the form of the free base, one or more tautomers thereof or a pharmaceutically acceptable acid addition salt thereof.

In an embodiment (E55) of embodiment (E1) the compound is selected from the compounds listed in Table 1.

In an embodiment (E56) of any of embodiments (E1) to (E55) the compound is for use as a medicament.

In an embodiment (E57) of any of embodiments (E1) to (E55) the compound is for use in the treatment of a disease selected from the group consisting of Alzheimer's disease, mental retardation; CIAS, attention-deficit/hyperactivity disorder; and age-related cognitive decline, substance-induced psychotic disorder, for example psychosis induced by alcohol, amphetamine, *cannabis*, cocaine, hallucinogens, inhalants, opioids, or phencyclidine.

In an embodiment (E58) of any of embodiments (E1) to (E55) the compound is for preparation of a medicament for use in the treatment of a disease selected from the group consisting of Alzheimer's disease, mental retardation; CIAS, attention-deficit/hyperactivity disorder; and age-related cognitive decline, substance-induced psychotic disorder, for example psychosis induced by alcohol, amphetamine, *cannabis*, cocaine, hallucinogens, inhalants, opioids, or phencyclidine.

Embodiment (E59) of the present invention covers a method of treating a subject suffering from a disease selected from the group consisting of Alzheimer's disease, mental retardation; CIAS, attention-deficit/hyperactivity disorder; and age-related cognitive decline, substance-induced psychotic disorder, for example psychosis induced by alcohol, amphetamine, *cannabis*, cocaine, hallucinogens, inhalants, opioids, or phencyclidine, which method comprises administering to said subject a compound of any of embodiments (E1)-(E55).

In an embodiment (E60) the present invention covers a pharmaceutical composition comprising a therapeutically effective amount of a compound of any of embodiments (E1) to (E55), and one or more pharmaceutically acceptable carriers, diluents and excipients.

In an embodiment (E61) of embodiment (E60) the pharmaceutical composition is for the treatment of a disease selected from the group consisting of Alzheimer's disease, mental retardation; CIAS, attention-deficit/hyperactivity disorder; and age-related cognitive decline, substance-induced psychotic disorder, for example psychosis induced by alcohol, amphetamine, *cannabis*, cocaine, hallucinogens, inhalants, opioids, or phencyclidine.

Table 1 lists compounds of the invention and the corresponding IC50 values (nM) determined as described in the section "PDE9 inhibition assay". Each of the compounds constitutes an individual embodiment of the present invention:

TABLE 1

Compounds of the invention and IC50 values

| Compound | Compound No. | IC50 (nM) |
|---|---|---|
| 3-(4-fluorophenyl)-6-[1-(3-methoxyazetidin-1-yl)ethyl]-7h-imidazo[1,5-a]pyrazin-8-one | 1 | 73 |
| 6-[1-(cyclohexylmethylamino)ethyl]-3-phenyl-7h-imidazo[1,5-a]pyrazin-8-one | 2 | 187 |
| 6-[(3-methoxyazetidin-1-yl)methyl]-3-phenyl-7h-imidazo[1,5-a]pyrazin-8-one | 3 | 90 |
| 3-phenyl-6-[(3-pyrazin-2-yloxyazetidin-1-yl)methyl]-7h-imidazo[1,5-a]pyrazin-8-one | 4 | 32 |
| 3-phenyl-6-[(3-pyrimidin-2-yloxyazetidin-1-yl)methyl]-7h-imidazo[1,5-a]pyrazin-8-one | 5 | 30 |
| 6-[[3-[(6-fluoro-2-pyridyl)oxy]azetidin-1-yl]methyl]-3-phenyl-7h-imidazo[1,5-a]pyrazin-8-one | 6 | 31 |
| 3-phenyl-6-[1-(3-pyrimidin-2-yloxyazetidin-1-yl)ethyl]-7h-imidazo[1,5-a]pyrazin-8-one | 7 | 14 |
| 3-phenyl-6-[(3-phenylazetidin-1-yl)methyl]-7h-imidazo[1,5-a]pyrazin-8-one | 8 | 78 |
| 6-[[benzyl(methyl)amino]methyl]-3-phenyl-7h-imidazo[1,5-a]pyrazin-8-one | 9 | 156 |
| methyl 1-benzyl-4-(8-oxo-3-phenyl-7h-imidazo[1,5-a]pyrazin-6-yl)pyrrolidine-3-carboxylate | 10 | 43 |
| 6-[[3-(4-ethylphenyl)azetidin-1-yl]methyl]-3-phenyl-7h-imidazo[1,5-a]pyrazin-8-one | 11 | 127 |
| 6-[1-[3-(4-fluorophenyl)azetidin-1-yl]propyl]-3-phenyl-7h-imidazo[1,5-a]pyrazin-8-one | 12 | 19 |
| 3-phenyl-6-[(3-quinoxalin-2-yloxyazetidin-1-yl)methyl]-7h-imidazo[1,5-a]pyrazin-8-one | 13 | 7 |
| 6-[[3-(4,6-dimethylpyrimidin-2-yl)oxyazetidin-1-yl]methyl]-3-phenyl-7h-imidazo[1,5-a]pyrazin-8-one | 14 | 50 |
| 3-phenyl-6-[1-(3-pyrazin-2-yloxyazetidin-1-yl)ethyl]-7h-imidazo[1,5-a]pyrazin-8-one | 15 | 40 |
| 6-[[3-(3-fluorophenoxy)azetidin-1-yl]methyl]-3-phenyl-7h-imidazo[1,5-a]pyrazin-8-one | 16 | 97 |
| 6-[(3-anilinopyrrolidin-1-yl)methyl]-3-phenyl-7h-imidazo[1,5-a]pyrazin-8-one | 17 | 28 |
| 3-phenyl-6-[1-(3-phenylazetidin-1-yl)ethyl]-7h-imidazo[1,5-a]pyrazin-8-one | 18 | 54 |
| 6-[[3-(4-fluorophenyl)azetidin-1-yl]methyl]-3-phenyl-7h-imidazo[1,5-a]pyrazin-8-one | 19 | 69 |
| 6-[1-(3-methoxyazetidin-1-yl)ethyl]-3-phenyl-7h-imidazo[1,5-a]pyrazin-8-one | 20 | 17 |
| 6-[(3-phenoxyazetidin-1-yl)methyl]-3-phenyl-7h-imidazo[1,5-a]pyrazin-8-one | 21 | 8 |
| 6-[(3-methoxyazetidin-1-yl)-phenyl-methyl]-3-phenyl-7h-imidazo[1,5-a]pyrazin-8-one | 22 | 37 |
| 6-[[3-(4-fluorophenoxy)azetidin-1-yl]methyl]-3-phenyl-7h-imidazo[1,5-a]pyrazin-8-one | 23 | 16 |
| 6-[1-[3-(3-fluorophenoxy)azetidin-1-yl]ethyl]-3-phenyl-7h-imidazo[1,5-a]pyrazin-8-one | 24 | 25 |
| 6-[1-(3-phenoxyazetidin-1-yl)ethyl]-3-phenyl-7h-imidazo[1,5-a]pyrazin-8-one | 25 | 28 |
| 6-[1-[3-(4-fluorophenoxy)azetidin-1-yl]ethyl]-3-phenyl-7h-imidazo[1,5-a]pyrazin-8-one | 26 | 19 |
| 6-[1-[3-[(6-fluoro-2-pyridyl)oxy]azetidin-1-yl]ethyl]-3-phenyl-7h-imidazo[1,5-a]pyrazin-8-one | 27 | 38 |
| 6-[1-[3-(4-fluorophenyl)azetidin-1-yl]ethyl]-3-phenyl-7h-imidazo[1,5-a]pyrazin-8-one | 28 | 53 |
| 6-[1-[3-(4-methyl-2-pyridyl)azetidin-1-yl]ethyl]-3-phenyl-7h-imidazo[1,5-a]pyrazin-8-one | 29 | 20 |
| 6-[1-[3-(4-ethylphenyl)azetidin-1-yl]ethyl]-3-phenyl-7h-imidazo[1,5-a]pyrazin-8-one | 30 | 16 |
| 6-(1-benzyl-4-methyl-pyrrolidin-3-yl)-3-phenyl-7h-imidazo[1,5-a]pyrazin-8-one | 31 | 33 |
| 6-[1-[3-(2-fluorophenoxy)azetidin-1-yl]ethyl]-3-phenyl-7h-imidazo[1,5-a]pyrazin-8-one | 32 | 72 |
| 6-[[3-(2-fluorophenoxy)azetidin-1-yl]methyl]-3-phenyl-7h-imidazo[1,5-a]pyrazin-8-one | 33 | 18 |
| 6-[1-[3-(4-methoxyphenyl)azetidin-1-yl]ethyl]-3-phenyl-7h-imidazo[1,5-a]pyrazin-8-one | 34 | 66 |
| 4-[1-[(8-oxo-3-phenyl-7h-imidazo[1,5-a]pyrazin-6-yl)methyl]azetidin-3-yl]benzonitrile | 35 | 49 |
| 3-phenyl-6-[1-(3-pyrimidin-2-ylazetidin-1-yl)ethyl]-7h-imidazo[1,5-a]pyrazin-8-one | 36 | 79 |
| 3-phenyl-6-[[3-(2-pyridyl)azetidin-1-yl]methyl]-7h-imidazo[1,5-a]pyrazin-8-one | 37 | 29 |
| 4-[1-[1-(8-oxo-3-phenyl-7h-imidazo[1,5-a]pyrazin-6-yl)ethyl]azetidin-3-yl]benzonitrile | 38 | 23 |
| 3-cyclopentyl-6-[(3-pyrimidin-2-yloxyazetidin-1-yl)methyl]-7h-imidazo[1,5-a]pyrazin-8-one | 39 | 22 |
| 3-cyclopentyl-6-[1-[3-(4-fluorophenyl)azetidin-1-yl]ethyl]-7h-imidazo[1,5-a]pyrazin-8-one | 40 | 5 |
| 3-cyclopentyl-6-[[3-(4-methoxyphenyl)azetidin-1-yl]methyl]-7h-imidazo[1,5-a]pyrazin-8-one | 41 | 26 |
| 3-cyclopentyl-6-[1-(3-pyrimidin-2-yloxyazetidin-1-yl)ethyl]-7h-imidazo[1,5-a]pyrazin-8-one | 42 | 8 |

TABLE 1-continued

Compounds of the invention and IC50 values

| Compound | Compound No. | IC50 (nM) |
|---|---|---|
| 6-[4-methyl-1-(2-pyridylmethyl)pyrrolidin-3-yl]-3-phenyl-7h-imidazo[1,5-a]pyrazin-8-one | 43 | 14 |
| 6-[[3-(4-fluorophenyl)azetidin-1-yl]methyl]-3-tetrahydropyran-4-yl-7h-imidazo[1,5-a]pyrazin-8-one | 44 | 25 |
| 6-[(3-benzyloxyazetidin-1-yl)methyl]-3-(4-fluorophenyl)-7h-imidazo[1,5-a]pyrazin-8-one | 45 | 1 |
| 3-cyclopentyl-6-[[3-(3-methylquinoxalin-2-yl)oxyazetidin-1-yl]methyl]-7h-imidazo[1,5-a]pyrazin-8-one | 46 | 6 |
| 3-cyclopentyl-6-[1-[3-(4-fluorophenoxy)azetidin-1-yl]ethyl]-7h-imidazo[1,5-a]pyrazin-8-one | 47 | 3 |
| 3-cyclopentyl-6-[[3-(4-dimethylaminophenyl)azetidin-1-yl]methyl]-7h-imidazo[1,5-a]pyrazin-8-one | 48 | 40 |
| 6-[[3-(2-fluorophenoxy)azetidin-1-yl]methyl]-3-(4-fluorophenyl)-7h-imidazo[1,5-a]pyrazin-8-one | 49 | 16 |
| 6-[[3-(2-fluorophenoxy)azetidin-1-yl]methyl]-3-tetrahydropyran-4-yl-7h-imidazo[1,5-a]pyrazin-8-one | 50 | 21 |
| 6-[[3-(4-dimethylaminophenyl)azetidin-1-yl]methyl]-3-(4-fluorophenyl)-7h-imidazo[1,5-a]pyrazin-8-one | 51 | 7 |
| 3-cyclopentyl-6-[1-[3-(2-fluorophenoxy)azetidin-1-yl]ethyl]-7h-imidazo[1,5-a]pyrazin-8-one | 52 | 49 |
| 3-(4-fluorophenyl)-6-[(3-pyrimidin-2-ylazetidin-1-yl)methyl]-7h-imidazo[1,5-a]pyrazin-8-one | 53 | 22 |
| 6-[(3-pyrimidin-2-ylazetidin-1-yl)methyl]-3-tetrahydropyran-4-yl-7h-imidazo[1,5-a]pyrazin-8-one | 54 | 102 |
| 3-(4-fluorophenyl)-6-[(3-pyrazin-2-yloxyazetidin-1-yl)methyl]-7h-imidazo[1,5-a]pyrazin-8-one | 55 | 9 |
| 6-[(3-benzyloxyazetidin-1-yl)methyl]-3-cyclopentyl-7h-imidazo[1,5-a]pyrazin-8-one | 56 | 50 |
| 3-cyclopentyl-6-[(3-isopropoxyazetidin-1-yl)methyl]-7h-imidazo[1,5-a]pyrazin-8-one | 57 | 17 |
| 3-cyclopentyl-6-[(3-isobutoxyazetidin-1-yl)methyl]-7h-imidazo[1,5-a]pyrazin-8-one | 58 | 4 |
| 3-cyclopentyl-6-[1-[3-(4-dimethylaminophenyl)azetidin-1-yl]ethyl]-7h-imidazo[1,5-a]pyrazin-8-one | 59 | 57 |
| 3-(4-fluorophenyl)-6-[[3-[(6-fluoro-2-pyridyl)oxy]azetidin-1-yl]methyl]-7h-imidazo[1,5-a]pyrazin-8-one | 60 | 164 |
| 3-(4-fluorophenyl)-6-[[3-(2-pyridyl)azetidin-1-yl]methyl]-7h-imidazo[1,5-a]pyrazin-8-one | 61 | 79 |
| 6-[[3-(2-pyridyl)azetidin-1-yl]methyl]-3-tetrahydropyran-4-yl-7h-imidazo[1,5-a]pyrazin-8-one | 62 | 78 |
| 6-[[3-(4-fluorophenoxy)azetidin-1-yl]methyl]-3-(4-fluorophenyl)-7h-imidazo[1,5-a]pyrazin-8-one | 63 | 13 |
| 3-tetrahydropyran-4-yl-6-[[3-[4-(trifluoromethoxy)phenoxy]azetidin-1-yl]methyl]-7h-imidazo[1,5-a]pyrazin-8-one | 64 | 13 |
| 6-[[3-[(6-fluoro-2-pyridyl)oxy]azetidin-1-yl]methyl]-3-tetrahydropyran-4-yl-7h-imidazo[1,5-a]pyrazin-8-one | 65 | 91 |
| 6-[(3-anilinopyrrolidin-1-yl)methyl]-3-tetrahydropyran-4-yl-7h-imidazo[1,5-a]pyrazin-8-one | 66 | 15 |
| 6-[(3-benzyloxyazetidin-1-yl)methyl]-3-tetrahydropyran-4-yl-7h-imidazo[1,5-a]pyrazin-8-one | 67 | 20 |
| 6-[(3-phenylazetidin-1-yl)methyl]-3-tetrahydropyran-4-yl-7h-imidazo[1,5-a]pyrazin-8-one | 68 | 8 |
| 6-[[3-(4-methoxyphenyl)azetidin-1-yl]methyl]-3-tetrahydropyran-4-yl-7h-imidazo[1,5-a]pyrazin-8-one | 69 | 30 |
| 3-tetrahydropyran-4-yl-6-[[3-[5-(trifluoromethyl)-2-pyridyl]azetidin-1-yl]methyl]-7h-imidazo[1,5-a]pyrazin-8-one | 70 | 10 |
| 6-[[3-(3-fluorophenoxy)azetidin-1-yl]methyl]-3-tetrahydropyran-4-yl-7h-imidazo[1,5-a]pyrazin-8-one | 71 | 7 |
| 6-[(3-quinoxalin-2-yloxyazetidin-1-yl)methyl]-3-tetrahydropyran-4-yl-7h-imidazo[1,5-a]pyrazin-8-one | 72 | 139 |
| 3-(4-fluorophenyl)-6-[(3-phenoxyazetidin-1-yl)methyl]-7h-imidazo[1,5-a]pyrazin-8-one | 73 | 177 |
| 3-(4-fluorophenyl)-6-[[3-[4-(trifluoromethoxy)phenoxy]azetidin-1-yl]methyl]-7h-imidazo[1,5-a]pyrazin-8-one | 74 | 16 |
| 6-[[3-(4-fluorophenoxy)azetidin-1-yl]methyl]-3-tetrahydropyran-4-yl-7h-imidazo[1,5-a]pyrazin-8-one | 75 | 115 |
| 3-(4-fluorophenyl)-6-[[3-(4-fluorophenyl)azetidin-1-yl]methyl]-7h-imidazo[1,5-a]pyrazin-8-one | 76 | 33 |
| 3-(4-fluorophenyl)-6-[[3-[5-(trifluoromethyl)-2-pyridyl]azetidin-1-yl]methyl]-7h-imidazo[1,5-a]pyrazin-8-one | 77 | 4 |
| 6-[[3-(4-ethylphenyl)azetidin-1-yl]methyl]-3-tetrahydropyran-4-yl-7h-imidazo[1,5-a]pyrazin-8-one | 78 | 6 |
| 6-[4-methyl-1-[[6-(trifluoromethyl)-3-pyridyl]methyl]pyrrolidin-3-yl]-3-tetrahydropyran-4-yl-7h-imidazo[1,5-a]pyrazin-8-one | 79 | 23 |

TABLE 1-continued

Compounds of the invention and IC50 values

| Compound | Compound No. | IC50 (nM) |
|---|---|---|
| 4-[1-[(8-oxo-3-tetrahydropyran-4-yl-7h-imidazo[1,5-a]pyrazin-6-yl)methyl]azetidin-3-yl]oxybenzonitrile | 80 | 18 |
| 6-[4-methyl-1-(2-pyridylmethyl)pyrrolidin-3-yl]-3-tetrahydropyran-4-yl-7h-imidazo[1,5-a]pyrazin-8-one | 81 | 19 |
| 6-[[3-(4-pyridyloxy)azetidin-1-yl]methyl]-3-tetrahydropyran-4-yl-7h-imidazo[1,5-a]pyrazin-8-one | 82 | 14 |
| 6-[[3-(3-pyridyloxy)azetidin-1-yl]methyl]-3-tetrahydropyran-4-yl-7h-imidazo[1,5-a]pyrazin-8-one | 83 | 36 |
| 6-[(3-pyrimidin-2-yloxypyrrolidin-1-yl)methyl]-3-tetrahydropyran-4-yl-7h-imidazo[1,5-a]pyrazin-8-one | 84 | 110 |
| 3-(4-fluorophenyl)-6-[(3-phenoxypyrrolidin-1-yl)methyl]-7h-imidazo[1,5-a]pyrazin-8-one | 85 | 140 |
| 3-(4-fluorophenyl)-6-[(3-pyrimidin-2-yloxypyrrolidin-1-yl)methyl]-7h-imidazo[1,5-a]pyrazin-8-one | 86 | 233 |
| 3-(4-fluorophenyl)-6-[[3-(4-pyridyloxy)azetidin-1-yl]methyl]-7h-imidazo[1,5-a]pyrazin-8-one | 87 | 42 |
| 3-(4-fluorophenyl)-6-[[3-(3-pyridyloxy)azetidin-1-yl]methyl]-7h-imidazo[1,5-a]pyrazin-8-one | 88 | 3 |
| 6-[1-[(4-fluorophenyl)methyl]-4-methyl-pyrrolidin-3-yl]-3-tetrahydropyran-4-yl-7h-imidazo[1,5-a]pyrazin-8-one | 89 | 7 |
| 6-[4-methyl-1-(pyrimidin-2-ylmethyl)pyrrolidin-3-yl]-3-tetrahydropyran-4-yl-7h-imidazo[1,5-a]pyrazin-8-one | 90 | 19 |
| 6-[1-(3-pyrimidin-2-ylazetidin-1-yl)ethyl]-3-tetrahydropyran-4-yl-7h-imidazo[1,5-a]pyrazin-8-one | 91 | 46 |
| 4-[1-[[3-(4-fluorophenyl)-8-oxo-7h-imidazo[1,5-a]pyrazin-6-yl]methyl]azetidin-3-yl]oxybenzonitrile | 92 | 76 |
| 3-[1-[[3-(4-fluorophenyl)-8-oxo-7h-imidazo[1,5-a]pyrazin-6-yl]methyl]azetidin-3-yl]oxybenzonitrile | 93 | 18 |
| 3-[1-[(8-oxo-3-tetrahydropyran-4-yl-7h-imidazo[1,5-a]pyrazin-6-yl)methyl]azetidin-3-yl]oxybenzonitrile | 94 | 12 |
| 3-(4-fluorophenyl)-6-[[3-[3-(trifluoromethyl)phenoxy]azetidin-1-yl]methyl]-7h-imidazo[1,5-a]pyrazin-8-one | 95 | 97 |
| 4-[1-[[3-(4-fluorophenyl)-8-oxo-7h-imidazo[1,5-a]pyrazin-6-yl]methyl]azetidin-3-yl]benzonitrile | 96 | 2 |
| 6-[4-methyl-1-(quinoxalin-6-ylmethyl)pyrrolidin-3-yl]-3-tetrahydropyran-4-yl-7h-imidazo[1,5-a]pyrazin-8-one | 97 | 4 |
| 4-[[3-methyl-4-(8-oxo-3-tetrahydropyran-4-yl-7h-imidazo[1,5-a]pyrazin-6-yl)pyrrolidin-1-yl]methyl]benzonitrile | 98 | 18 |
| 3-(4-fluorophenyl)-6-[1-[(4-fluorophenyl)methyl]-4-methyl-pyrrolidin-3-yl]-7h-imidazo[1,5-a]pyrazin-8-one | 99 | 17 |
| 1-bromo-3-(4-fluorophenyl)-6-[1-[(4-fluorophenyl)methyl]-4-methyl-pyrrolidin-3-yl]-7h-imidazo[1,5-a]pyrazin-8-one | 100 | 4 |
| 6-[1-[(6-methoxy-3-pyridyl)methyl]-4-methyl-pyrrolidin-3-yl]-3-tetrahydropyran-4-yl-7h-imidazo[1,5-a]pyrazin-8-one | 101 | 18 |
| 6-[4-methyl-1-[(5-methylpyrazin-2-yl)methyl]pyrrolidin-3-yl]-3-tetrahydropyran-4-yl-7h-imidazo[1,5-a]pyrazin-8-one | 102 | 10 |
| 6-[[3-[(4-fluorophenyl)methoxy]azetidin-1-yl]methyl]-3-tetrahydropyran-4-yl-7h-imidazo[1,5-a]pyrazin-8-one | 103 | 21 |
| 3-tetrahydropyran-4-yl-6-[[3-[4-(trifluoromethyl)phenoxy]azetidin-1-yl]methyl]-7h-imidazo[1,5-a]pyrazin-8-one | 105 | 109 |
| 3-cyclopentyl-1,5-difluoro-6-[(3-phenylazetidin-1-yl)methyl]-7h-imidazo[1,5-a]pyrazin-8-one | 105 | 33 |
| 4-[1-[(8-oxo-3-tetrahydropyran-4-yl-7h-imidazo[1,5-a]pyrazin-6-yl)methyl]azetidin-3-yl]benzonitrile | 106 | 32 |
| 3-[1-[(8-oxo-3-tetrahydropyran-4-yl-7h-imidazo[1,5-a]pyrazin-6-yl)methyl]azetidin-3-yl]benzonitrile | 107 | 35 |
| 6-[[3-[(4-chlorophenyl)methoxy]azetidin-1-yl]methyl]-3-(4-fluorophenyl)-7h-imidazo[1,5-a]pyrazin-8-one | 108 | 34 |
| 3-(4-fluorophenyl)-6-[[3-[4-(trifluoromethyl)phenoxy]azetidin-1-yl]methyl]-7h-imidazo[1,5-a]pyrazin-8-one | 109 | 28 |
| 3-(4-chlorophenyl)-6-[1-[(4-fluorophenyl)methyl]-4-methyl-pyrrolidin-3-yl]-7h-imidazo[1,5-a]pyrazin-8-one | 110 | 36 |
| 1-bromo-3-(4-chlorophenyl)-6-[1-[(4-fluorophenyl)methyl]-4-methyl-pyrrolidin-3-yl]-7h-imidazo[1,5-a]pyrazin-8-one | 111 | 74 |
| 6-[1-(3-methoxyazetidin-1-yl)ethyl]-6-methyl-3-tetrahydropyran-4-yl-7h-imidazo[1,5-a]pyrazin-8-one | 112 | 22 |
| 3-(4-fluorophenyl)-6-[[3-(p-tolylmethoxy)azetidin-1-yl]methyl]-7h-imidazo[1,5-a]pyrazin-8-one | 113 | 9 |
| 3-(4-fluorophenyl)-6-[4-methyl-1-(2-pyridylmethyl)pyrrolidin-3-yl]-7h-imidazo[1,5-a]pyrazin-8-one | 114 | 7 |
| 6-[1-(cyclohexylmethyl)-4-methyl-pyrrolidin-3-yl]-3-tetrahydropyran-4-yl-7h-imidazo[1,5-a]pyrazin-8-one | 115 | 37 |
| 3-(4-fluorophenyl)-6-[1-(3-isopropoxyazetidin-1-yl)ethyl]-7h-imidazo[1,5-a]pyrazin-8-one | 116 | 22 |

TABLE 1-continued

Compounds of the invention and IC50 values

| Compound | Compound No. | IC50 (nM) |
|---|---|---|
| 6-[1-(3-isopropoxyazetidin-1-yl)ethyl]-3-tetrahydropyran-4-yl-7h-imidazo[1,5-a]pyrazin-8-one | 117 | 93 |
| 6-[[3-(4-chlorophenoxy)azetidin-1-yl]methyl]-3-(4-fluorophenyl)-7h-imidazo[1,5-a]pyrazin-8-one | 118 | 42 |
| 6-[1-[(4-fluorophenyl)methyl]-4-methyl-pyrrolidin-3-yl]-3-[4-(trifluoromethoxy)phenyl]-7h-imidazo[1,5-a]pyrazin-8-one | 119 | 191 |
| 3-(4-fluorophenyl)-6-[1-[3-[4-(trifluoromethoxy)phenoxy]azetidin-1-yl]ethyl]-7h-imidazo[1,5-a]pyrazin-8-one | 120 | 35 |
| 6-[[3-(2,6-difluorophenoxy)azetidin-1-yl]methyl]-3-(4-fluorophenyl)-7h-imidazo[1,5-a]pyrazin-8-one | 121 | 41 |
| 3-(3,5-difluorophenyl)-6-[[3-(4-methoxyphenyl)azetidin-1-yl]methyl]-7h-imidazo[1,5-a]pyrazin-8-one | 122 | 38 |
| 3-(4-fluorophenyl)-6-[[3-(4-methoxyphenyl)azetidin-1-yl]methyl]-7h-imidazo[1,5-a]pyrazin-8-one | 123 | 57 |
| 3-(4-fluorophenyl)-6-[1-[3-(4-fluorophenyl)azetidin-1-yl]ethyl]-7h-imidazo[1,5-a]pyrazin-8-one | 124 | 72 |
| 3-tetrahydrofuran-3-yl-6-[[3-[3-(trifluoromethyl)phenyl]pyrrolidin-1-yl]methyl]-7h-imidazo[1,5-a]pyrazin-8-one | 125 | 48 |
| 3-(4-fluorophenyl)-6-[1-[3-(4-methoxyphenyl)azetidin-1-yl]ethyl]-7h-imidazo[1,5-a]pyrazin-8-one | 126 | 70 |
| 3-(4,4-difluorocyclohexyl)-6-[[3-(4-methoxyphenyl)azetidin-1-yl]methyl]-7h-imidazo[1,5-a]pyrazin-8-one | 127 | n.d. |
| 3-(4,4-difluorocyclohexyl)-6-[(3-methoxyazetidin-1-yl)methyl]-7h-imidazo[1,5-a]pyrazin-8-one | 128 | n.d. |
| 6-[[3-(4-fluorophenoxy)azetidin-1-yl]methyl]-3-tetrahydrofuran-3-yl-7h-imidazo[1,5-a]pyrazin-8-one | 129 | n.d. |

DEFINITION OF SUBSTITUENTS

As used in the context of the present invention, the terms "halo" and "halogen" are used interchangeably and refer to fluorine, chlorine, bromine or iodine. The term "$C_1$-$C_6$ alkyl" refers to a straight-chain or branched saturated hydrocarbon having from one to six carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, and n-hexyl. The expression "$C_1$-$C_6$ hydroxyalkyl" refers to a $C_1$-$C_6$ alkyl group as defined above which is substituted with one hydroxy group.

The term "halo($C_1$-$C_6$)alkyl" refers to a $C_1$-$C_6$ alkyl group as defined above which is substituted with up to three halogen atoms, such as trifluoromethyl.

The expression "$C_1$-$C_6$ alkoxy" refers to a straight-chain or branched saturated alkoxy group having from one to six carbon atoms, inclusive, with the open valency on the oxygen. Examples of such groups include, but are not limited to, methoxy, ethoxy, n-butoxy, 2-methyl-pentoxy and n-hexyloxy.

The term "$C_3$-$C_8$ cycloalkyl" typically refers to cyclopropyl, cyclobutyl, cyclopentyl, cyclohexyl, cycloheptyl or cyclooctyl.

The expression "$C_1$-$C_6$ alkyl($C_3$-$C_8$)cycloalkyl" refers to a $C_3$-$C_8$ cycloalkyl as defined above which is substituted with a straight-chain or branched $C_1$-$C_6$ alkyl. Examples of such groups include, but are not limited to, cyclopropylmethyl.

The term "heterocycloalkyl" refers to a four to eight membered ring containing carbon atoms and up to three N, O or S atoms, provided that the four to eight membered ring does not contain adjacent O or adjacent S atoms. The open valency is on either the heteroatom or carbon atom. Examples of such groups include, but are not limited to, azetidinyl, oxetanyl, piperazinyl, morpholinyl, thiomorpholinyl and [1,4]diazepanyl.

The term "hydroxyheterocycloalkyl" refers to a heterocycloalkyl as defined above which is substituted with one hydroxy group.

The term "$C_1$-$C_6$ alkyl-heterocycloalkyl" refers to a heterocycloalkyl as defined above which is substituted with a $C_1$-$C_6$ alkyl group. Examples of such groups include, but are not limited to, tetrahydropyran-4-yl-methyl and 2-morpholin-4-yl-ethyl.

The term "aryl" refers to a phenyl ring, optionally substituted with halogen, $C_1$-$C_6$ alkyl, $C_1$-$C_6$ alkoxy or halo($C_1$-$C_6$)alkyl as defined above. Examples of such groups include, but are not limited to, phenyl and 4-chlorophenyl.

The term "$C_1$-$C_6$arylalkyl" refers to an aryl as defined above which is substituted with a straight-chain or branched $C_1$-$C_6$ alkyl. Examples of such groups include, but are not limited to, benzyl and 4-chlorobenzyl.

The term aryloxy refers to an univalent radical of the form Ar—O (such as phenoxy) composed of an aryl group (Ar) united with oxygen (O).

The term heteroaryloxy refers to an aryloxy where one or more carbon atoms have been substituted with one more hetero atoms, such as N, O, S.

In the context of the present invention the term 'cyclization point' is understood to mean that connecting the atoms indicated to be cyclization points by a bond results in a cyclic structure (a ring). The cyclization point is indicated with a * in the illustrative reaction scheme below:

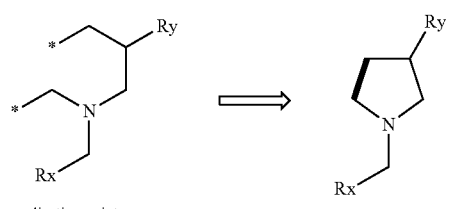

* Denotes cyclization points

Additionally, the present invention further provides certain embodiments of the invention, which are described below. Additionally, the present invention further provides certain embodiments of the invention that are described below.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., J. Pharm. Sci. 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Pharmaceutical Composition

The present invention further provides a pharmaceutical composition comprising a therapeutically effective amount of a compound of formula (I) and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising admixing a therapeutically effective amount of a compound of formula (I) and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. One example is an acid addition salt of a compound having the utility of a free base. When a compound of formula (I) contains a free base such salts are prepared in a conventional manner by treating a solution or suspension of a free base of formula (I) with a molar equivalent of a pharmaceutically acceptable acid. Representative examples of suitable organic and inorganic acids are described above.

For parenteral administration, solutions of the compounds of formula (I) in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of formula (I) may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of formula (I) and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Diseases

In a particular embodiment the PDE9 inhibitors of the present invention may be used in the treatment of cognition deficiencies related to neurodegenerative disorders, such dementia, such as cortical dementia or subcortical dementia.

Cortical dementias arise from a disorder affecting the cerebral cortex, the outer layers of the brain that play a critical role in cognitive processes such as memory and language. Particularly considered cortical dementias are Alzheimer's disease; vascular dementia (also known as multi-infarct dementia), including Binswanger's disease; Dementia with Lewy bodies (DLB); Alcohol-Induced Persisting Dementia, including Korsakoffs syndrome and Wernicke's encephalopathy; frontotemporal lobar degeneration (FTLD), including: Pick's disease, frontotemporal dementia (or frontal variant FTLD), semantic dementia (or temporal variant FTLD), and progressive non-fluent aphasia; Creutzfeldt-Jakob disease; dementia pugilistica; Moyamoya disease; and posterior cortical atrophy (an Alzheimer's disease variant).

Subcortical dementias result from dysfunction in the parts of the brain that are beneath the cortex. Usually, the memory loss and language difficulties that are characteristic of cortical dementias are not present. Rather, people with subcortical dementias, such as Huntington's disease, Parkinson's Disease, and AIDS dementia complex, tend to show changes in their personality and attention span, and their thinking slows down. Particularly considered subcortical dementias are dementia due to Huntington's disease, dementia due to hypothyroidism, dementia due to Parkinson's disease, dementia due to Vitamin B1 deficiency, dementia due to Vitamin B12 deficiency, dementia due to folate deficiency, dementia due to syphilis, dementia due to subdural hematoma, dementia due to hypercalcaemia, dementia due to hypoglycaemia, AIDS dementia complex, pseudodementia (a major depressive episode with prominent cognitive symptoms), substance-induced persisting dementia, dementia due to multiple etiologies, dementia due to other general medical conditions (i.e. end stage renal failure, cardiovascular disease etc.), dementia not otherwise specified (used in cases where no specific criteria is met).

EXPERIMENTAL

Synthesis of Compound I

Compounds of formula (I) can be made by halogenation of a compound of formula IX with NCS, NBS, or NIS, in solvents such as acetonitrile or chloroform (Scheme 1):

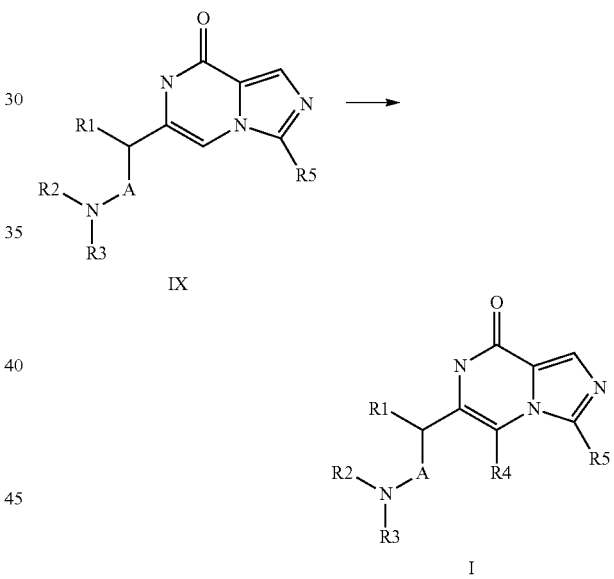

Compounds of formula IX, where A is $(CH_2)n$, n=0, and R1 is H, can be prepared by coupling of a electrophile of formula VI, where X is a leaving group, such as Cl, Br, I, or methanesulfonyl or 4-toluenesulfonyl, with an amine; compounds of formula VI can be synthesized by demethylation with HCl or $BBr_3$ of compounds of formula V. Compounds of formula V, where X is a halogen, can be prepared by halogenation of formula IV with $SOCl_2$, $PBr_3$. Compounds of formula VI, where X is methanesulfonyl or 4-toluenesulfonyl, can be synthesized by reaction of compounds of formula IV with methylsulfonyl chloride or 4-toluenesulfonyl chloride. Compounds of formula IV can be prepared by reduction with $NaBH_4$, LAH, DIBAL, $BH_3$, etc, of compounds of formula III, which can be made by carbonylation of compounds of formula II in the presence of CO, and a palladium catalyst, such as $Pd(dppf)Cl_2$, $Pd(PPh_3)_2Cl_2$, $Pd(PPh_3)_4$, and a base, such as $Cs_2CO_3$, $K_2CO_3$, or $Et_3N$ (Scheme 2):

Scheme 2

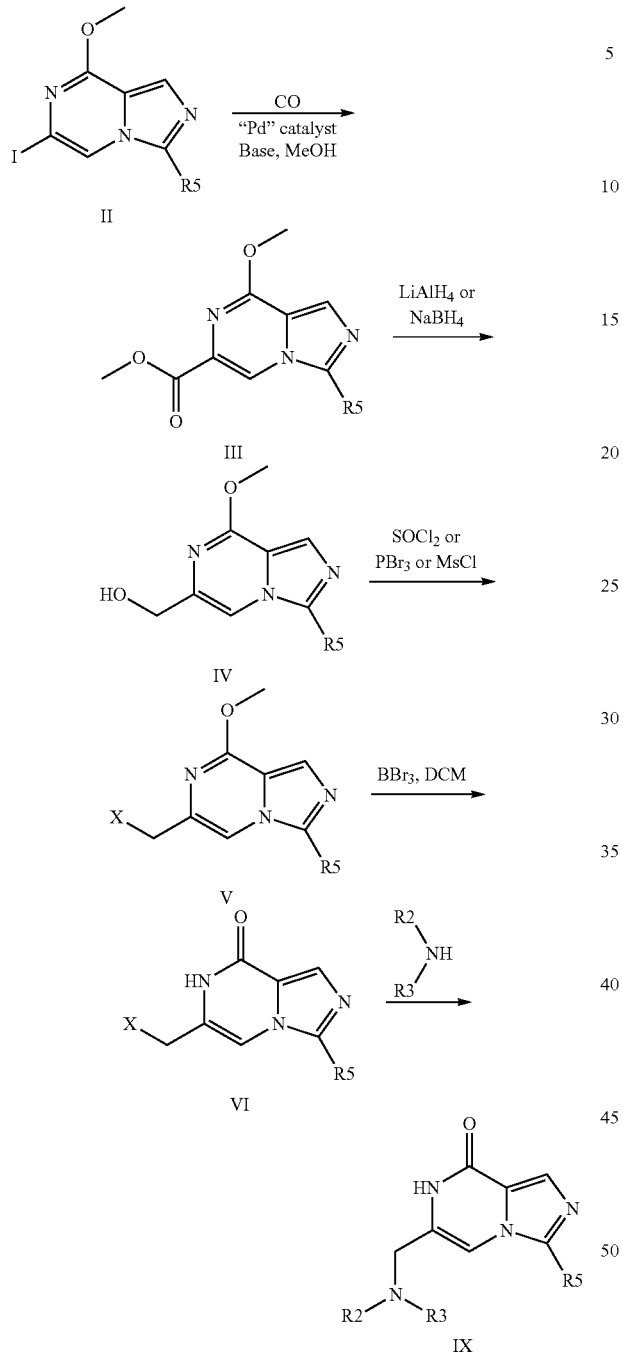

Scheme 3

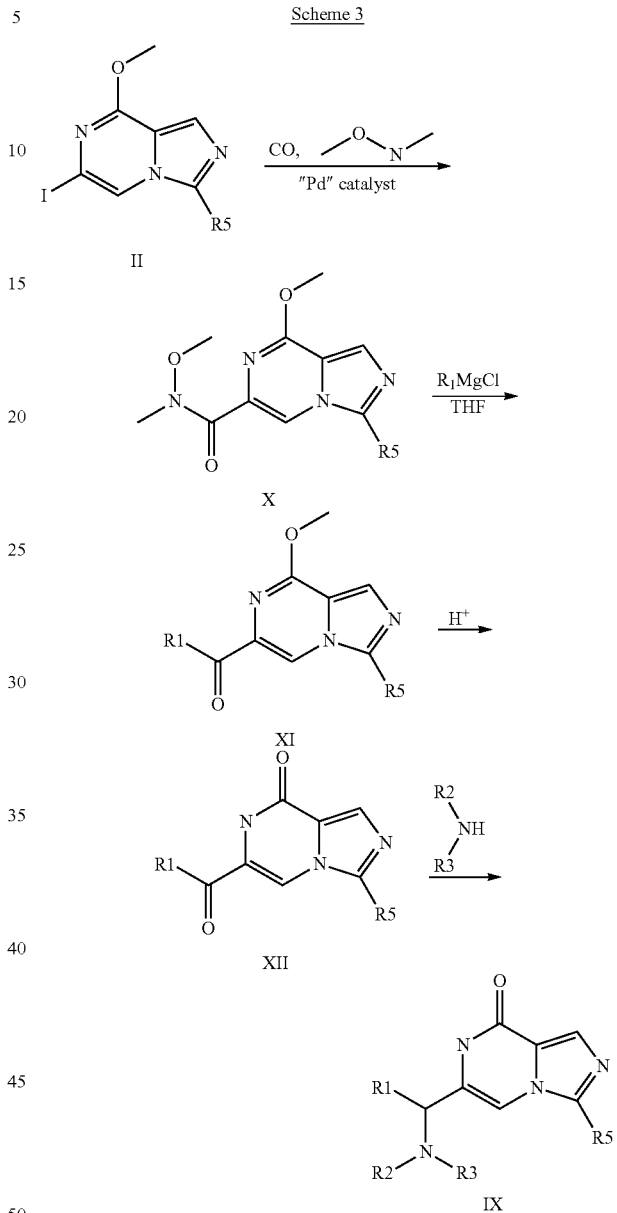

Cs₂CO₃, K₂CO₃, Et₃N, KOAc, etc., in solvents, such as toluene, DMF, DMSO (Scheme 3):

Compounds of formula IX, where A is (CH$_2$)n, n=0, and R1 is any alkyl, aryl groups, can be prepared by reductive amination of compounds of formula XII with various amines in the presence of Na(OAc)$_3$BH or Na(CN)BH$_3$ in solvents such as 1,2-dichloro ethane, CH$_2$Cl$_2$, methanol with a few drops of HOAc. Compounds of formula XII can be prepared by acid catalyzed demethylation of compounds of formula XI, which can be made from reaction of Weinreb amides of formula X with a Grignard reagent. Compounds of formula X can be made by carbonylation of compounds of formula II with CO in the presence of a palladium catalyst, such as Pd(dppf)Cl$_2$, Pd(PPh$_3$)$_4$, Pd(PPh$_3$)$_2$Cl$_2$, and a base, such as Compounds of formula IX, where A is (CH$_2$)n, n=1, R1 and R2 are connected to form a pyrrolidine, can be prepared by reductive amination of compounds of formula XX with various aldehydes in the presence of Na(OAc)$_3$BH or Na(CN)BH$_3$ in solvents such as 1,2-dichloro ethane, CH$_2$Cl$_2$, with a few drops of HOAc; or by alkylation of compounds of formula XX with a variety of alkyl or substituted alkyl halides in the presence of Cs$_2$CO$_3$ or K$_2$CO$_3$ in solvents such as DMF or 1,4-dioxane, etc. Compounds of formula XX can be prepared by hydrogenation of compounds of formula XIX, with H$_2$ and in the presence of Pd/C or Pd(OH)$_2$/C in solvents such as alcohol or EtOAc, etc. Compounds of formula XIX can be synthesized by mesylation of compounds of formula XVI, followed by reductive deoxygenation with NaBH$_4$ or LiAlH$_4$, and acid catalyzed demethylation. Compounds of formula XVI can be made by reduction with LAH, NaBH₄, DIBAL, etc, of compounds of formula XV, which can be made by [3+2] cycloaddtion of compounds of formula XIV with benzyl-methoxymethyl-trimethylsilanylmethylamine with the aid of TFA in solvents such as toluene or CH₂Cl₂. Compounds of formula XIV can be made by Suzuki reaction of compounds of formula II with boronic ester XIII in the presence of a palladium catalyst, such as Pd(dppf)Cl₂, Pd(PPh₃)₄, Pd(PPh₃)₂Cl₂, etc., and a base, such as Cs₂CO₃, K₂CO₃, KOAc, etc., in solvent, such as toluene, DMF, DMSO, etc; or by Heck reaction of compounds of formula II with ethyl acrylate in the presence of a palladium catalyst, such as Pd(dppf)Cl₂, Pd(PPh₃)₄, Pd(PPh₃)₂Cl₂ and a base, such as Cs₂CO₃, K₂CO₃, KOAc, etc. Boronic ester XIII can be generated by coupling of ethyl propiolate with bis(pinacolato)diboron in the presence of CuCl, and Xantphos as catalysts, t-BuOK as a base in the solvent of THF (Scheme 4):

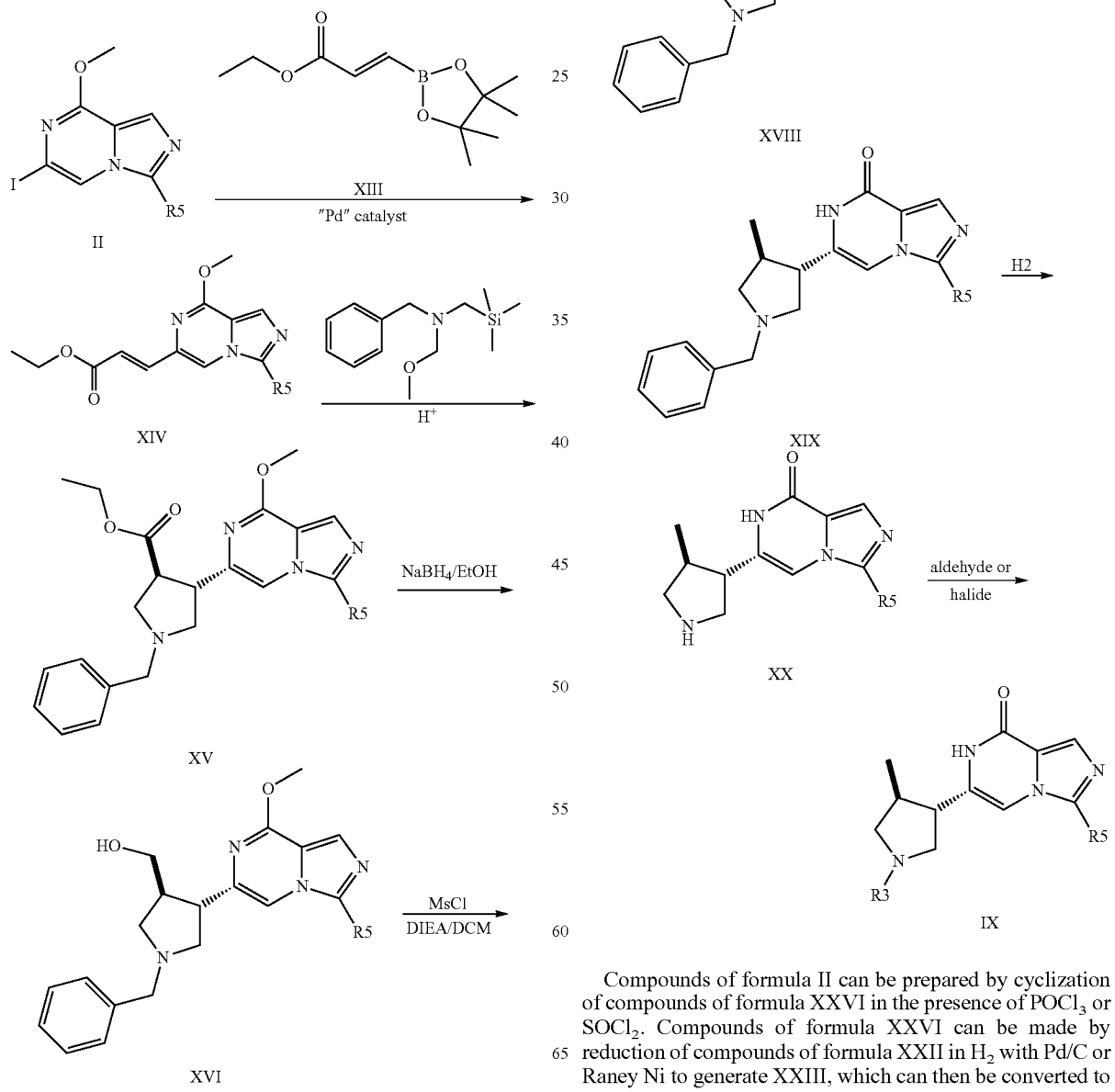

Compounds of formula II can be prepared by cyclization of compounds of formula XXVI in the presence of POCl₃ or SOCl₂. Compounds of formula XXVI can be made by reduction of compounds of formula XXII in H₂ with Pd/C or Raney Ni to generate XXIII, which can then be converted to amides of formula XXIV by reaction with a variety of acid chlorides, or by coupling with various carboxylic acids in the presence of coupling reagents, such as HOBt and EDC, or HATU. Subsequent deprotection under acidic conditions yields compounds of formula XXV, which can undergo diazotization and iodination. Compounds of formula XXII can be made from Boc protection of compounds of formula XXI (Scheme 5):

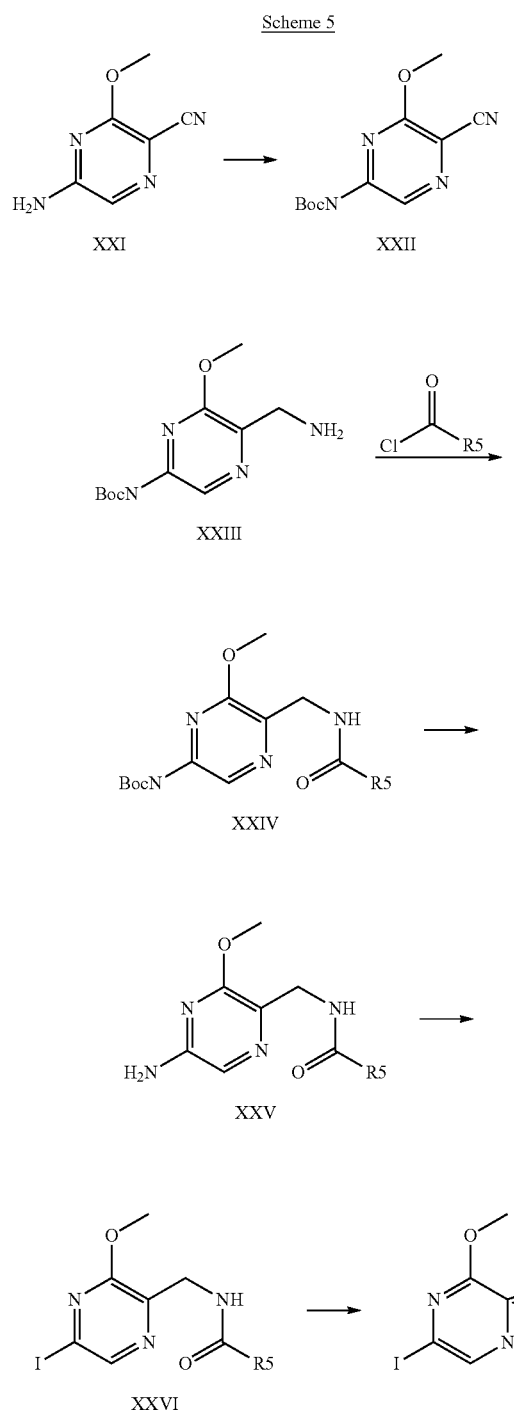

Synthesis of specific compounds is described in the Example section below.

EXAMPLES

Preparation of Intermediates tert-butyl 5-(aminomethyl)-6-methoxypyrazin-2-ylcarbamate

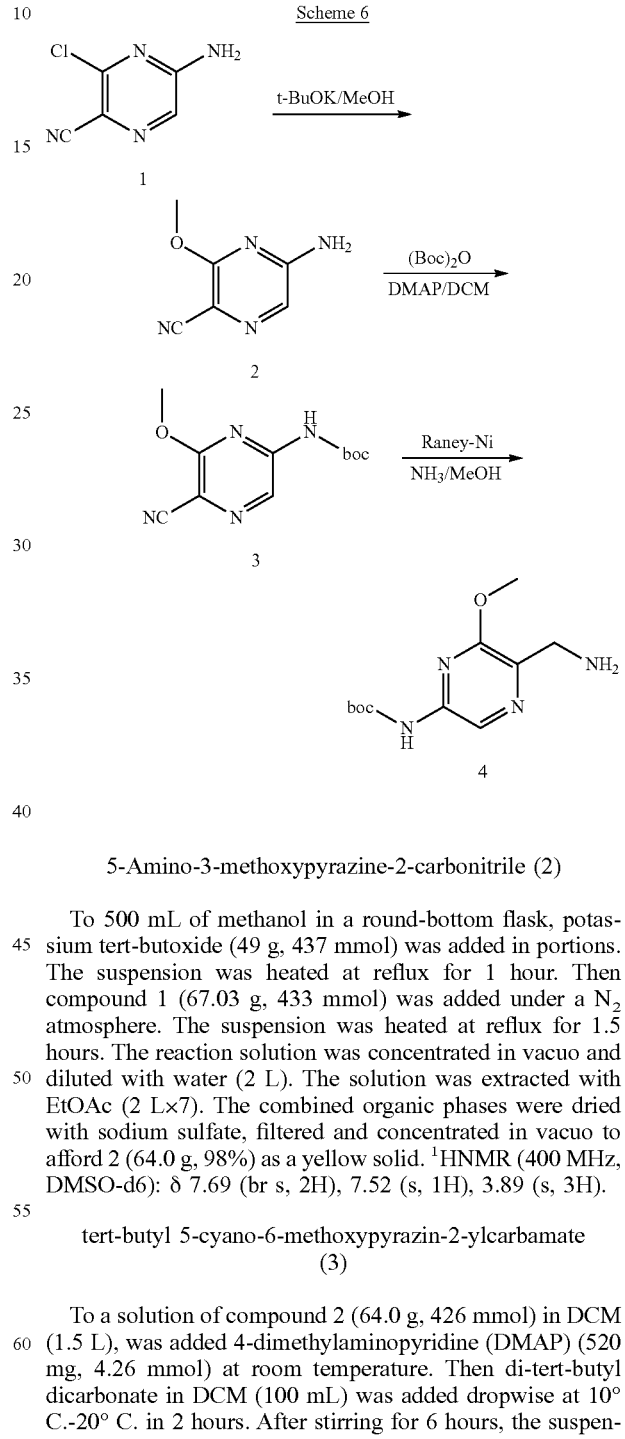

5-Amino-3-methoxypyrazine-2-carbonitrile (2)

To 500 mL of methanol in a round-bottom flask, potassium tert-butoxide (49 g, 437 mmol) was added in portions. The suspension was heated at reflux for 1 hour. Then compound 1 (67.03 g, 433 mmol) was added under a $N_2$ atmosphere. The suspension was heated at reflux for 1.5 hours. The reaction solution was concentrated in vacuo and diluted with water (2 L). The solution was extracted with EtOAc (2 L×7). The combined organic phases were dried with sodium sulfate, filtered and concentrated in vacuo to afford 2 (64.0 g, 98%) as a yellow solid. $^1$HNMR (400 MHz, DMSO-d6): δ 7.69 (br s, 2H), 7.52 (s, 1H), 3.89 (s, 3H).

tert-butyl 5-cyano-6-methoxypyrazin-2-ylcarbamate (3)

To a solution of compound 2 (64.0 g, 426 mmol) in DCM (1.5 L), was added 4-dimethylaminopyridine (DMAP) (520 mg, 4.26 mmol) at room temperature. Then di-tert-butyl dicarbonate in DCM (100 mL) was added dropwise at 10° C.-20° C. in 2 hours. After stirring for 6 hours, the suspension turned clear and it was diluted with 500 mL of water. The organic phase was separated, dried over sodium sulfate and concentrated in vacuo. The residue was purified by column chromatography on silica gel (eluted with petroleum ether/EtOAc=10:1) to afford 3 (46.5 g, 44%). ¹HNMR (400 MHz, CDCl₃): δ 8.93 (s, 1H), 7.25 (s, 1H), 3.99 (s, 3H), 1.55 (s, 9H).

tert-butyl
5-(aminomethyl)-6-methoxypyrazin-2-ylcarbamate
(4)

To a solution of compound 3 (30.0 g, 120 mmol) in NH₃/methanol (500 mL) at room temperature, was added Raney Ni (10 g). The resulting suspension was stirred under an atmosphere of H₂ overnight. It was diluted with a 1:1 mixture of DCM and methanol. The solution was filtered and the filtrate was concentrated in vacuo. The residue was washed with methanol to afford 4 (19.5 g, 64%) as a white solid. ¹HNMR (400 MHz, CDCl₃): δ 8.66 (s, 1H), 6.90 (s, 1H), 3.98 (s, 3H), 3.48 (s, 2H), 1.55 (s, 9H).

6-Chloromethyl-3-phenyl-7H-imidazo[1,5-a]pyrazin-8-one

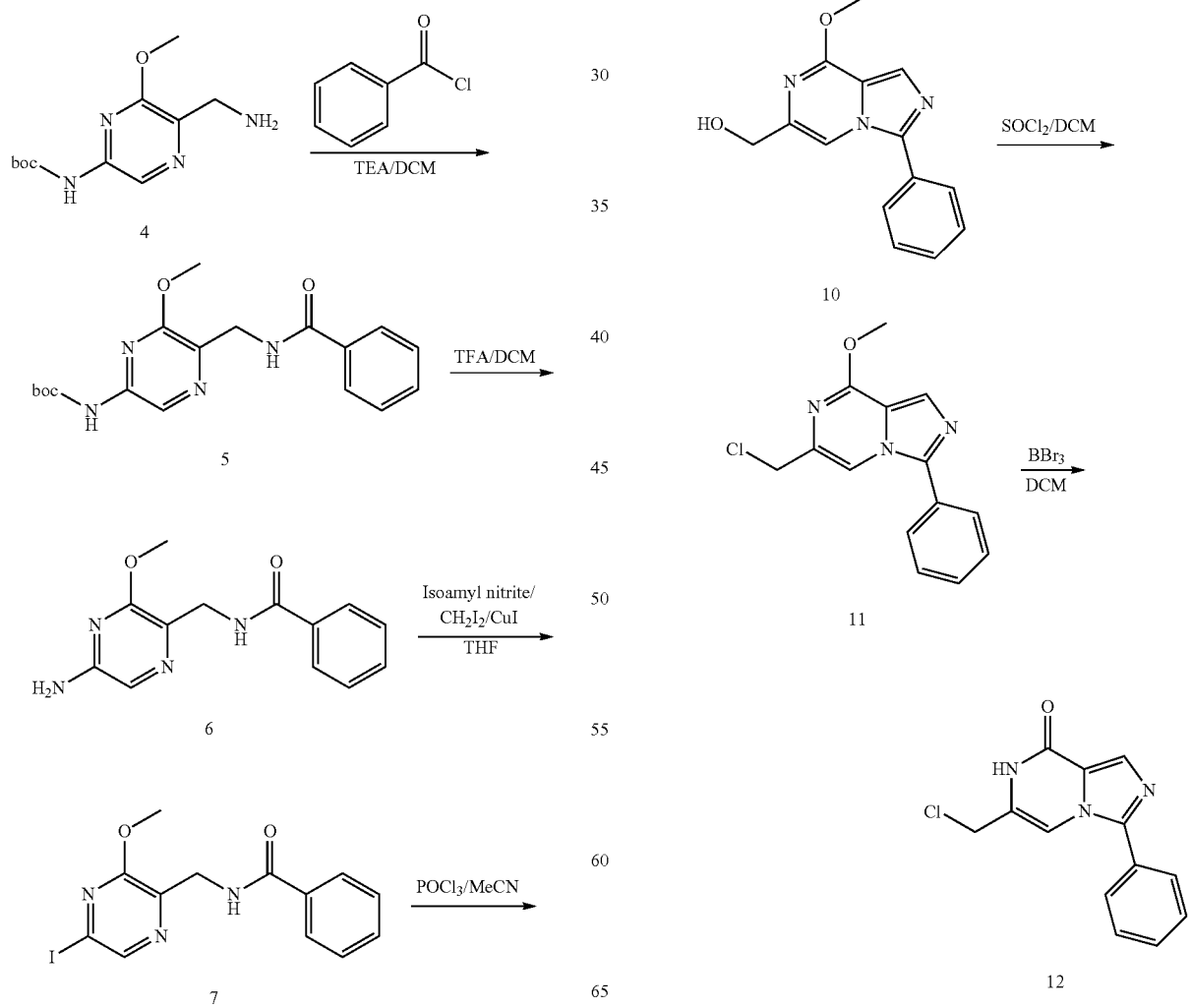

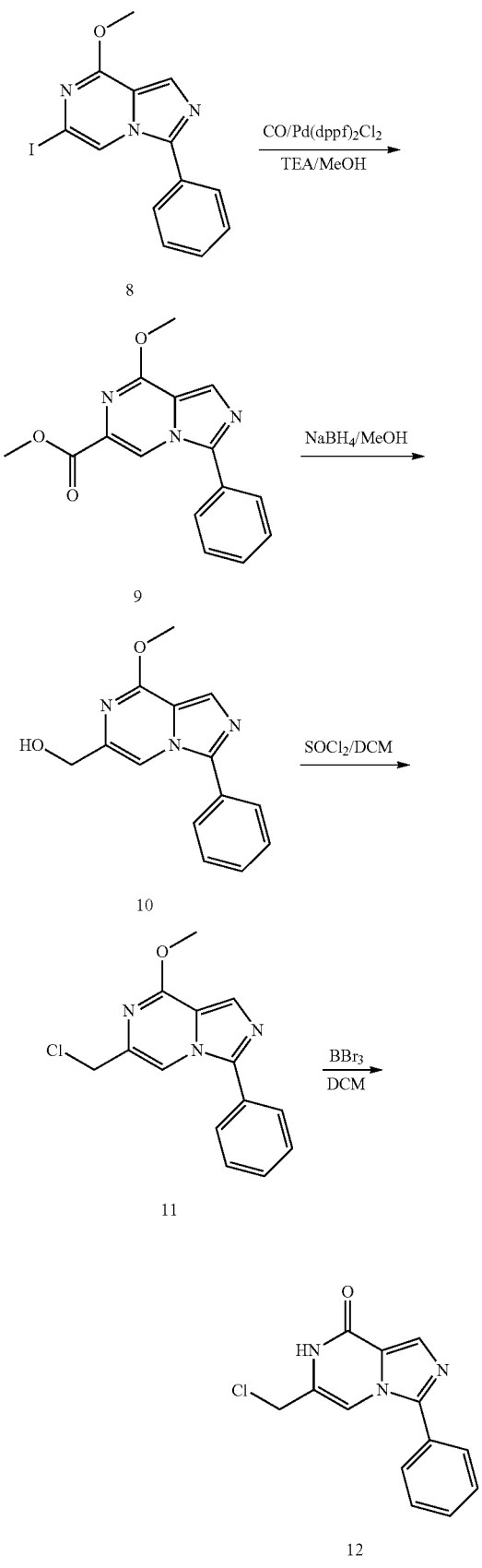

tert-butyl 5-(benzamidomethyl)-6-methoxypyrazin-2-ylcarbamate (5)

To a solution of compound 4 (19.5 g, 76.7 mmol) in DCM (200 mL) was added TEA (23 g, 230 mmol), followed by dropwise addition of benzoyl chloride (11.8 g, 84.3 mmol) at 0° C. The resulting reaction mixture was stirred at room temperature for 2 hours. The reaction was monitored by TLC. Upon completion, the reaction was quenched with water (100 mL). The organic phase was separated and the aqueous phase was extracted with DCM (200 mL×2). The combined organic phases were dried over anhydrous MgSO$_4$, filtered and concentrated in vacuo. The residue was purified by column chromatography on silica gel to afford 5 (21.7 g, 78.9%) as a yellow solid. $^1$HNMR (400 MHz, CDCl$_3$): δ 8.70 (s, 1H), 7.88 (d, J=6.8 Hz, 2H), 7.62 (br s, 1H), 7.44-7.52 (m, 3H), 6.95 (s, 1H), 4.68 (d, J=4.4 Hz, 2H), 3.93 (s, 3H), 1.54 (s, 9H).

N-((5-amino-3-methoxypyrazin-2-yl)methyl)benzamide (6)

To as solution of compound 5 (21.7 g, 60.5 mmol) in DCM (100 mL), was added TFA (100 mL). The reaction was stirred at room temperature overnight. The solvent was removed. The residue was taken up in a mixture of DCM (100 mL) and saturated aqueous NaHCO$_3$ solution (100 mL). The organic phase was separated and the aqueous phase was extracted with DCM (100 mL×2). The combined organic phases were dried over anhydrous MgSO$_4$, filtered and concentrated in vacuo. The residue was purified by column chromatography on silica gel (eluted with petroleum ether/EtOAc=6:1 to 1:1) to afford 6 (10.0 g, 64%) as a yellow solid. $^1$HNMR (400 MHz, CDCl$_3$): δ 8.56 (t, J=5.2 Hz, 1H), 7.86 (d, J=7.2 Hz, 2H), 7.43-7.53 (m, 3H), 7.36 (s, 1H), 6.25 (br s, 2H), 4.38 (d, J=5.2 Hz, 2H), 3.92 (s, 3H).

N-((5-iodo-3-methoxypyrazin-2-yl)methyl)benzamide (7)

To a solution of compound 6 (4.5 g, 17.4 mmol) in anhydrous THF (100 mL), were added CuI (3.3 g, 17.4 mmol), isoamyl nitrite (6.1 g, 52.2 mmol) and CH$_2$I$_2$ (4.7 g, 17.4 mmol) respectively under a N$_2$ atmosphere. The reaction mixture was heated at 75° C. for 5 hours. Then the reaction was cooled down to room temperature and filtered. The filtrate was concentrated in vacuo. The residue was purified by column chromatography on silica gel (eluted with petroleum ether/EtOAc 5:1) to afford 7 (6.2 g, 96%) as a pale yellow solid. $^1$HNMR (400 MHz, CDCl$_3$): δ 8.35 (s, 1H), 7.87 (d, J=7.2 Hz, 2H), 7.44-7.52 (m, 4H), 4.68 (d, J=4.4 Hz, 2H), 4.04 (s, 3H).

6-Iodo-8-methoxy-3-phenylimidazo[1,5-a]pyrazine (8)

To a suspension of compound 7 (7.9 g, 21.4 mmol) in CH$_3$CN (200 mL), was added POCl$_3$ (32.7 g, 214 mmol) under a N$_2$ atmosphere and the reaction mixture was heated at 85° C. for 6 hours. The solvent was removed under reduced pressure. The residue was diluted with a mixture of DCM (100 mL) and ice-water (30 mL), followed by the saturated aqueous Na$_2$CO$_3$ solution (100 mL). The organic phase was separated and the aqueous phase was extracted with DCM (100 mL×2). The combined organic phases were dried, filtered and concentrated in vacuum. The residue was purified by column chromatography on silica gel (eluted with petroleum ether/EtOAc=20:1 to 3:1) to afford 8 (3.6 g, 47.9%) as a yellow solid. $^1$HNMR (400 MHz, CD$_3$OD): δ 8.51 (s, 1H), 8.34 (s, 1H), 7.87-7.89 (m, 2H), 7.77-7.79 (m, 3H), 4.22 (s, 3H).

Methyl 8-methoxy-3-phenylimidazo[1,5-a]pyrazine-6-carboxylate (9)

To a mixture of 8 (3.0 g, 8.54 mmol), CuI (460 mg, 2.4 mmol) and Pd(dppf)$_2$Cl$_2$ (670 mg, 0.8 mmol) in methanol (50 mL) was added TEA (6 mL) and then it was heated at 85° C. under 3.0 MPa CO for 16 hours. The reaction was allowed to cool to room temperature, concentrated in vacuo to give the crude product. The residue was purified by column chromatography on silica gel (eluted with petroleum ether/EtOAc=1:1) to afford 9 (2.1 g, 86%). $^1$H NMR (400 MHz, CDCl$_3$): δ 8.66 (s, 1H), 7.87 (s, 1H), 7.80 (m, 2H), 7.53-7.60 (m, 3H), 4.20 (s, 3H), 3.95 (s, 3H).

(8-methoxy-3-phenylimidazo[1,5-a]pyrazin-6-yl)methanol (10)

To a solution of 9 (2.0 g, 7.06 mmol) in methanol (60 mL) was added NaBH$_4$ (2.6 g, 70.6 mmol) in portions at 0° C. After addition, the mixture was stirred at room temperature for 5 hours. The reaction was quenched with water (100 mL) and concentrated in vacuo. Then the resulting mixture was extracted with EtOAc (150 mL×2). The combined organic phases were washed with water and then brine, dried over sodium sulfate, filtered and concentrated in vacuo. The residue was purified by column chromatography on silica gel (eluted with petroleum ether/EtOAc=3:1) to give 10 (1.2 g, 63%). $^1$H NMR (400 MHz, DMSO-d6): δ 7.92 (s, 1H), 7.82-7.84 (m, 3H), 7.51-7.60 (m, 2H), 5.39 (t, J=5.2 Hz, 1H), 4.42 (d, J=4.4 Hz, 2H), 4.03 (s, 3H).

6-(chloromethyl)-8-methoxy-3-phenylimidazo[1,5-a]pyrazine (11)

To a solution of 10 (1.2 g, 4.47 mmol) in dichloromethane (60 mL) was added dropwise sulfurous oxychloride (3.0 mL) under ice-water bath cooling. After the addition, the mixture was stirred for another 2 hours. The reaction was quenched with ice-water, washed with brine, dried over sodium sulfate, filtered and concentrated in vacuo to afford 11 (920 mg, 75%). $^1$H NMR (400 MHz, DMSO-d6): δ 8.36 (s, 1H), 7.84-7.87 (m, 3H), 7.54-7.62 (m, 3H), 4.72 (s, 2H), 4.06 (s, 3H).

6-Chloromethyl-3-phenyl-7H-imidazo[1,5-a]pyrazin-8-one (12)

To a solution of 11 (900 mg, 3.29 mmol) in dichloromethane (100 mL), was added dropwise boron tribromide (8.2 g, 32.9 mmol) at 0° C., and it was stirred at room temperature overnight. The reaction was quenched with water (60 mL), and then concentrated in vacuo to remove dichloromethane. pH of the solution was adjusted to 8 with saturated aqueous NaHCO$_3$ solution, followed by extraction with DCM (200 mL×2). The combined organic phases were dried over anhydrous MgSO$_4$, filtered and dried to the desired product 12 (750 mg, 87%). $^1$H NMR (400 MHz, DMSO-d6): δ 7.88 (s, 1H), 7.75-7.79 (m, 3H), 7.55-7.60 (m, 3H), 4.58 (s, 2H).

6-Acetyl-3-phenyl-7H-imidazo[1,5-a]pyrazin-8-one

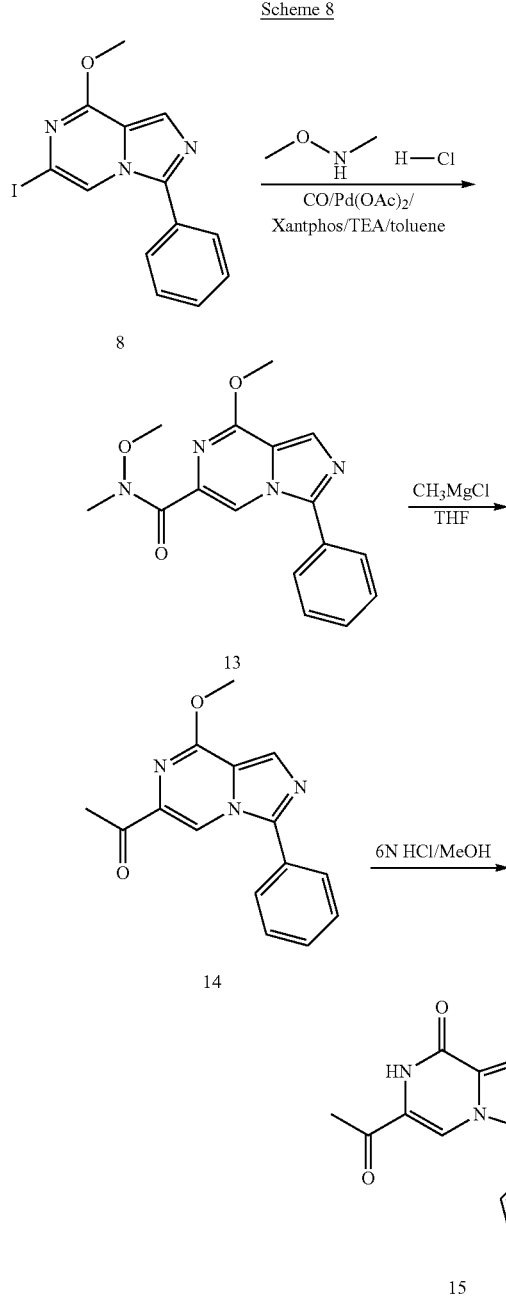

1-(8-Methoxy-3-phenyl-imidazo[1,5-a]pyrazin-6-yl)-ethanone (14)

To a solution of compound 13 (1.8 g, 5.76 mmol) in THF (100 mL) was dropwise added $CH_3MgCl$ (11.7 mL, 2 M, 23.4 mmol) at −78° C. After addition, the mixture was stirred at −30° C. for 3 h. The reaction was quenched with aq. $NH_4Cl$ solution (60 mL), extracted with EtOAc (50×3 mL). The combined organic phases were washed with brine (60 mL), dried over $Na_2SO_4$, concentrated in vacuo. The residue was purified by column chromatography on silica gel (eluted with EtOAc/petroleum ether=10:1) to afford compound 14 (1.46 g, 95%) as a yellow solid. $^1H$ NMR (400 MHz, $CDCl_3$): δ 8.59 (s, 1H), 7.87 (s, 1H), 7.78-7.80 (m, 2H), 7.51-7.58 (m, 3H), 4.18 (s, 3H), 2.66 (s, 3H).

6-Acetyl-3-phenyl-7H-imidazo[1,5-a]pyrazin-8-one (15)

To a solution of compound 14 (400 mg, 1.5 mmol) in methanol (15 mL) was added 6N HCl (aq.) solution (10 mL). The result solution was stirred at 60° C. for 16 h. The reaction mixture was concentrated in vacuo to dryness to afford compound 15 (320 mg, 84%) as a white solid. $^1H$ NMR (400 MHz, DMSO-d6): δ 10.55 (s, 1H), 8.15 (s, 1H), 8.02 (s, 1H), 7.89-7.91 (m, 2H), 7.60-7.65 (m, 3H), 2.51 (s, 3H).

3-Phenyl-azetidine Hydrochloride (A1)

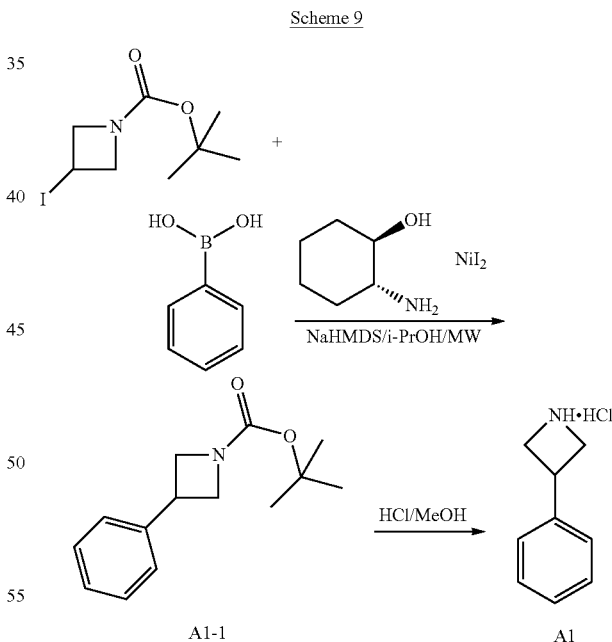

8-Methoxy-3-phenyl-imidazo[1,5-a]pyrazine-6-carboxylic acid methoxy-methyl-amide (13)

To a solution of compound 8 (1.56 g, 4.46 mmol) and N,O-dimethyl hydroxylamine hydrochloride (870 mg, 8.92 mmol) in toluene (80 mL) was added $Pd(OAc)_2$ (200 mg, 0.89 mmol), Xantphos (514 mg, 0.89 mmol) and TEA (2.5 mL, 17.8 mmol). The resulting solution was stirred at 90° C. for 16 h under an atmosphere of CO. The reaction mixture was cooled down and filtered. The filtrate was concentrated in vacuo. The residue was purified by column chromatography on silica gel (eluted with EtOAc/petroleum ether=1:2 to 2:1) to afford compound 13 (0.91 g, 65%) as a red solid.

An adaption of the method described by Matthew A. J., *Organci Letters.*, 2008, Vol. 10, No. 15, 3259-3262 was used. A microwave vial was charged with phenylboronic acid (244 mg, 2.0 mmol), $NiI_2$ (18.8 mg, 0.06 mmol), trans-2-aminocyclohexanol hydrochloride (9.1 mg, 0.06 mmol) and sodium hexamethyldisilazane (1 mL, 2 M in THF, 2.0 mmol). Isopropyl alcohol (2 mL) was added under a nitrogen atmosphere and the mixture was stirred for 5-10 minutes. The solution of 1-Boc-3-iodoazetidine (283 mg, 1.0 mmol) in 0.5 mL of isopropyl alcohol was then added. The resulting mixture was stirred at 80° C. for 30 min under microwave irradiation. Then it was cooled to room temperature, and the mixture was diluted with ethanol (10 mL). The reaction mixture was filtered, and the filtrate was concentrated in vacuo. The residue was purified by column chromatography on silica gel (eluted with EtOAc/petroleum ether=1:5) to afford tert-butyl-3-Phenylazetidine-1-carboxylate A1-1 (120 mg, 52%) as an oil. $^1$H NMR (400 MHz, CDCl$_3$): δ 7.25-7.37 (m, 5H), 4.30-4.34 (m, 2H), 3.91-3.99 (m, 2H), 3.73-3.75 (m, 1H), 1.46 (s, 9H).

To a solution of tert-butyl-3-Phenylazetidine-1-carboxylate (A1-1) (120 mg, 0.515 mmol) in methanol (10 mL) was added aqueous HCl (conc.) solution (5 mL). The resulting solution was stirred at 25° C. for 6 h. The reaction mixture was concentrated in vacuo to dryness to afford 3-phenyl-azetidine hydrochloride A1 (80 mg, 92%) as a white solid without purification. $^1$H NMR (400 MHz, CD$_3$OD): δ 7.39-7.40 (m, 4H), 7.31-7.32 (m, 1H), 4.37-4.39 (m, 2H), 4.23-4.25 (m, 3H).

The following intermediates were prepared in a similar way:

3-(4-Ethyl-phenyl)-azetidine Hydrochloride (A2)

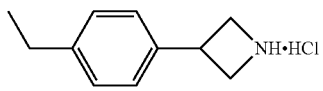

98% yield, $^1$H NMR (400 MHz, CD$_3$OD): δ 7.26-7.34 (m, 4H), 4.35-4.41 (m, 2H), 4.21-4.32 (m, 3H), 2.63-2.69 (dd, J=15.2, 7.6 Hz, 2H), 1.22-1.25 (t, J=7.6 Hz, 3H).

3-(4-Fluoro-phenyl)-azetidine Hydrochloride (A3)

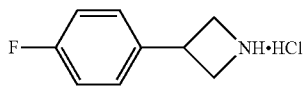

97% yield, $^1$H NMR (400 MHz, CD$_3$OD): δ 7.44-7.47 (m, 2H), 7.14-7.18 (m, 2H), 4.38-4.41 (m, 2H), 4.24-4.29 (m, 3H).

2-(Azetidin-3-yloxy)-pyrazine Hydrochloride (A4)

Scheme 10

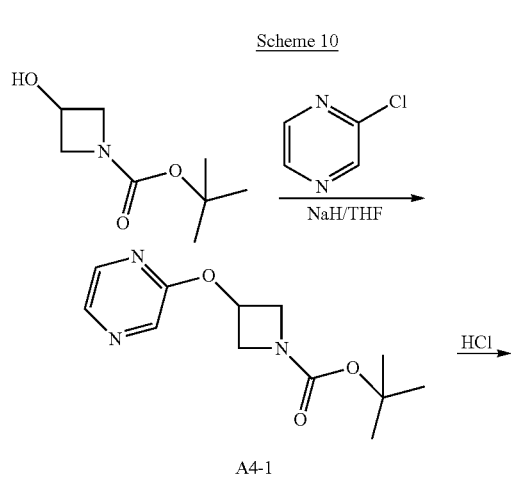

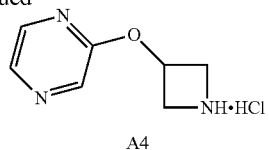

To a solution of 3-hydroxy-azetidine-1-carboxylic acid tert-butyl ester (0.8 g, 4.6 mmol) in THF (50 mL) was added sodium hydride (60% in mineral oil) (0.74 g, 18.5 mmol). The solution was stirred at 25° C. for 0.5 h, followed by addition of 2-chloro-pyrazine. The reaction mixture was heated at reflux overnight. The reaction solution was cooled to room temperature before water (50 ml) was added. It was then extracted with DCM (30 mL×3) and the combined organic phases were dried over anhydrous Na$_2$SO$_4$. The solution was filtered and the filtrate was concentrated in vacuo. The residue was purified by column chromatography on silica gel (eluted with DCM/EtOAc=100:1 to 2:1) to afford compound A4-1 (0.97 g, 84%). $^1$H NMR (400 MHz, CDCl$_3$): δ 8.28 (s, 1H), 8.17 (m, 1H), 8.05 (m, 1H), 5.30-5.33 (m, 1H), 4.32-4.36 (m, 2H), 3.98-4.01 (m, 2H), 1.45 (s, 9H).

To a solution of compound A4-1 (0.97 g, 3.8 mmol) in methanol (30 mL) was added concentrated hydrochloric acid (5 mL). The result solution was stirred at 25° C. for 3 h. The reaction mixture was concentrated in vacuo to dryness to afford the hydrochloric acid salt of 2-(Azetidin-3-yloxy)-pyrazine A4 (0.70 g, 97%). $^1$H NMR (400 MHz, D$_2$O): δ 8.25-8.40 (m, 3H), 5.55-5.59 (m, 1H), 4.58-4.63 (m, 2H), 4.28-4.32 (m, 2H).

The following intermediates were prepared in a similar way:

2-(Azetidin-3-yloxy)-pyrimidine Hydrochloride (A5)

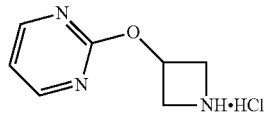

100% yield, $^1$H NMR (400 MHz, D$_2$O): δ 8.65 (d, J=5.2 Hz, 2H), 7.30-7.32 (m, 1H), 5.56-5.59 (m, 1H), 4.57-4.62 (m, 2H), 4.29-4.33 (m, 2H).

2-(Azetidin-3-yloxy)-6-fluoro-pyridine Hydrochloride (A6)

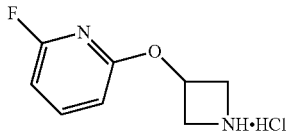

98% yield, $^1$H NMR (400 MHz, D$_2$O): δ 7.85-7.91 (m, 1H), 6.79-6.81 (m, 1H), 6.70-6.72 (m, 1H), 5.42-5.45 (m, 1H), 4.57-4.61 (m, 2H), 4.23-4.29 (m, 2H).

2-(Azetidin-3-yloxy)-4,6-dimethyl-pyrimidine Hydrochloride (A7)

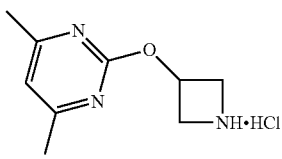

97% yield, $^1$H NMR (400 MHz, D$_2$O): δ 7.20 (s, 1H), 5.63-5.66 (m, 1H), 4.51-4.59 (m, 2H), 4.27-4.32 (m, 2H), 2.49 (s, 6H).

2-(Azetidin-3-yloxy)-quinoxaline Hydrochloride (A8)

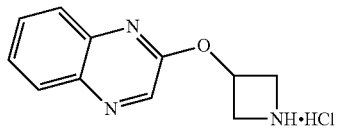

95% yield, $^1$H NMR (400 MHz, D$_2$O): δ 8.26 (s, 1H), 7.70 (d, J=8.4 Hz, 1H), 7.49-7.59 (m, 3H), 5.46-5.49 (m, 1H), 4.54-4.59 (dd, J=6.8, 12.8 Hz, 2H), 4.20-4.24 (dd, J=4.8, 12.8 Hz, 2H).

3-Methoxy-azetidine Hydrochloride (A9)

Scheme 11

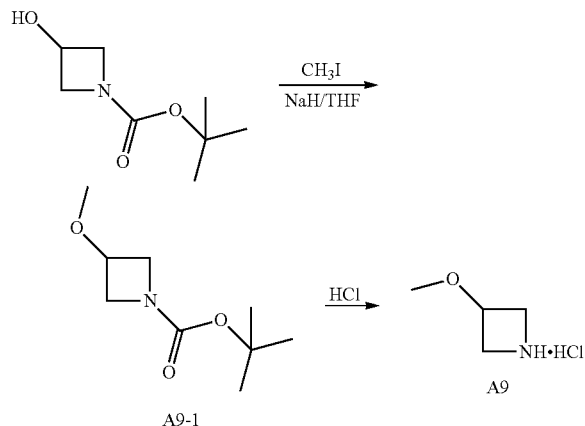

To a solution of 3-hydroxy-azetidine-1-carboxylic acid tert-butyl ester (0.8 g, 4.62 mmol) in THF (50 mL) was added sodium hydride (60% in mineral oil) (0.74 g, 18.5 mmol). The solution was stirred at 0° C. for 0.5 hour, followed by addition of iodomethane (2.8 mL, 46.2 mmol). The reaction mixture was stirred at room temperature overnight. The reaction was quenched with water (50 ml), and extracted with EtOAc (30 mL×3). The combined organic phases was dried over Na$_2$SO$_4$, filtered and concentrated in vacuo to afford compound A9-1 (0.8 g, 93%) as an oil. $^1$H NMR (400 MHz, CDCl$_3$): δ 4.11-4.13 (m, 1H), 4.04-4.08 (m, 2H), 3.79-3.83 (m, 2H), 3.27 (s, 3H), 1.43 (s, 9H).

To a solution of compound A9-1 (0.8 g, 4.29 mmol) in methanol (20 mL) was added concentrated hydrochloric acid (5 mL). The resulting solution was stirred at 25° C. for 16 h. The reaction mixture was concentrated in vacuum to dryness to afford the hydrochloric acid salt of 3-methoxy-azetidine A9 (0.48 g, 92%). $^1$H NMR (400 MHz, DMSO-d6): δ 9.56 (s, 1H), 4.22-4.25 (m, 1H), 4.06-4.10 (m, 2H), 3.74-3.79 (m, 2H), 3.21 (s, 3H).

3-(3-Fluoro-phenoxy)-azetidine Hydrochloride (A10)

Scheme 12

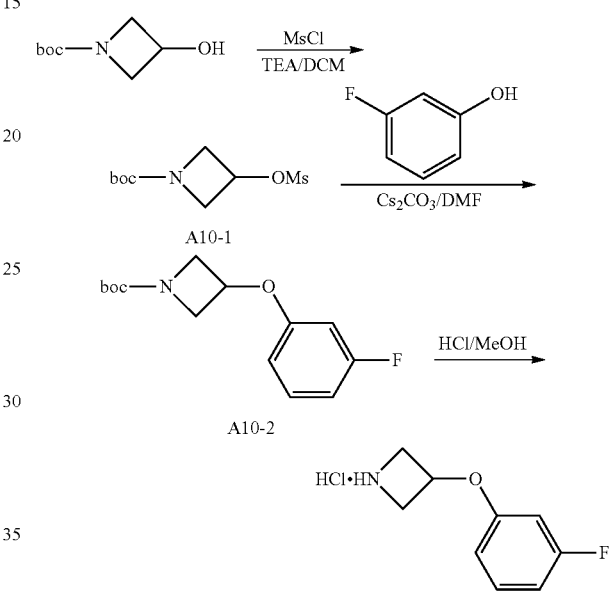

To a solution of 3-Hydroxy-azetidine-1-carboxylic acid tert-butyl ester (2.0 g, 11.2 mmol) and Et$_3$N (3.12 ml, 22.4 mmol) in DCM (20 ml) was added MsCl (0.92 ml, 11.6 mmol) dropwise at 0° C. The reaction mixture was stirred at room temperature overnight. The reaction mixture was diluted with brine (20 ml) and was extracted with ethyl acetate (20 mL×2). The combined organic layers was dried over anhydrous Na$_2$SO$_4$, filtered and concentrated in vacuum. The crude product was purified by column chromatography on silica gel (eluted with petroleum ether/EtOAc=10:1 to 2:1) to give compound A10-1 (2.0 g, 68%).

To a solution of A10-1 (0.795 g, 3.16 mmol) in DMF (20 ml) were added 3-fluorophenol (0.357 g, 3.16 mmol) and Cs$_2$CO$_3$ (1.13 g, 3.48 mmol). The reaction was stirred at 80° C. for 12 h until TLC showed that A10-1 had disappeared. The reaction mixture was diluted with brine (20 mL) and extracted with ethyl acetate (30 mL×2). The combined organic layers were dried over anhydrous Na$_2$SO$_4$, filtered and concentrated in vacuo. The residue was purified by column chromatography on silica gel (eluted with petroleum ether/EtOAc=10:1 to 2:1) to afford A10-2 (0.35 g, 41%)

To a solution of A10-2 (0.35 g, 1.31 mmol) in methanol (10 mL) was added concentrated hydrochloric acid (5 mL). The mixture was stirred at room temperature for 2 h. The solvent was evaporated to give desired product A10 (190 mg, 95%). $^1$H NMR (400 MHz, CDCl$_3$): δ 7.32-7.38 (m, 1H), 6.72-6.88 (m, 3H), 5.07-5.10 (m, 1H), 4.41-4.46 (m, 2H), 3.95-3.97 (m, 2H)

The following intermediates were prepared in a similar way:

3-(4-Fluoro-phenoxy)-azetidine Hydrochloride (A11)

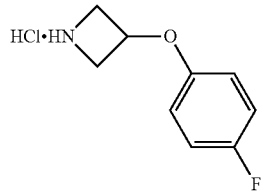

92% yield, $^1$H NMR (400 MHz, CDCl$_3$): δ 7.13-7.18 (d, J=8.8 Hz, 2H), 6.88-6.91 (m, 2H), 5.02-5.05 (m, 1H), 4.39-4.40 (m, 2H), 3.94-3.95 (m, 2H).

3-(Phenoxy)-azetidine Hydrochloride (A12)

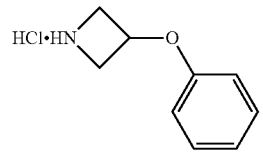

99% yield, $^1$H NMR (400 MHz, CDCl$_3$): δ 7.30-7.34 (dd, J=7.6, 8.0 Hz, 2H), 7.00-7.04 (m, 1H), 6.85-6.87 (d, J=8.0 Hz, 2H), 5.05-5.08 (m, 1H), 4.40-4.44 (m, 2H), 3.92-4.00 (m, 2H).

3-(2-Fluoro-phenoxy)-azetidine Hydrochloride (A13)

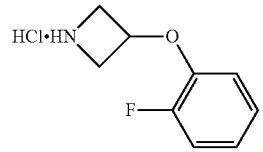

95% yield, $^1$H NMR (400 MHz, CDCl$_3$): δ 7.26-7.31 (m, 1H), 7.11-7.15 (m, 1H), 6.96-7.05 (m, 2H), 5.09-5.13 (m, 1H), 4.42-4.43 (m, 2H), 4.01-4.02 (m, 2H).

Phenyl-pyrrolidin-3-yl-amine Hydrochloride (A14)

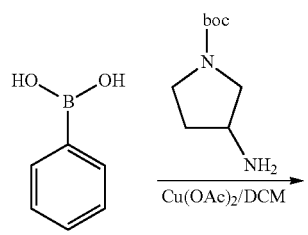

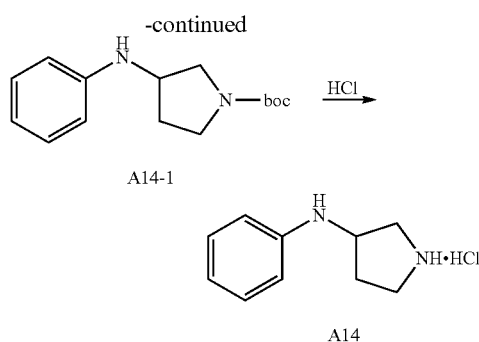

To a solution of phenylboronic acid (500 mg, 4.1 mmol) and 3-amino-pyrrolidine-1-carboxylic acid tert-butyl ester (760 mg, 4.1 mmol) in DCM (50 mL) at room temperature, was added cupric acetate (746 mg, 4.1 mmol). The suspension was stirred at room temperature overnight. The reaction mixture was filtered and the filtrate was concentrated in vacuo. The residue was purified by column chromatography on silica gel (eluted with petroleum ether/EtOAc=10:1) to afford A14-1 (160 mg, 15%).

To a solution of compound A14-1 (160 mg, 0.61 mmol) in methanol (20 mL) was added concentrated hydrochloric acid (5 mL). The reaction mixture was stirred at room temperature overnight, followed by concentration in vacuo. The residue was diluted with saturated aqueous NaHCO$_3$ solution (50 mL) and extracted with DCM (100 mL×3). The organic phases were dried with sodium sulfate and concentrated in vacuum to afford brown solid of A14 (80 mg, 56%)$^1$H NMR (400 MHz, CDCl$_3$): δ 9.86 (br s, 1H), 7.25-7.27 (m, 2H), 6.89 (t, J=7.2 Hz, 1H), 6.76-6.78 (d, J=8 Hz, 2H), 5.10 (br s, 1H), 4.30 (s, 1H), 3.34-3.51 (m, 4H), 2.33 (m, 1H), 2.18 (m, 1H).

Preparation of target compounds:

Example 1

3-Phenyl-6-(3-phenyl-azetidin-1-ylmethyl)-7H-imidazo-[1,5-a]pyrazin-8-one

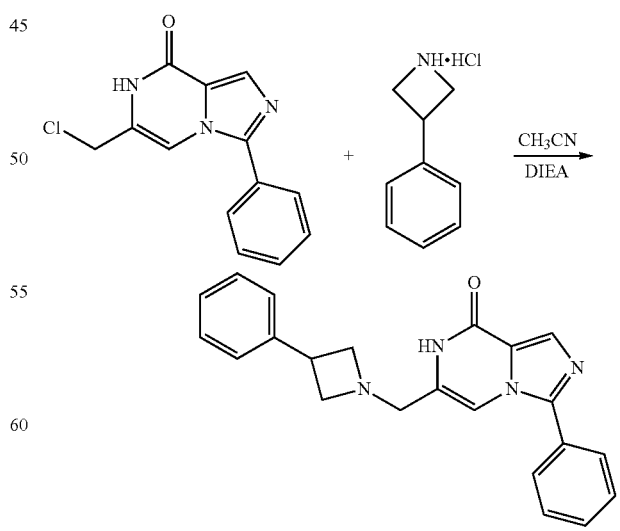

To a 50 mL round bottom flask, were charged compound 12 (50 mg, 0.192 mmol), 3-phenyl-azetidine hydrochloride (A1) (65 mg, 0.384 mmol), N,N-diisopropylethylamine (0.1 mL, 0.576 mmol) and acetonitrile (5 mL). The resulting solution was heated at reflux for 2 h. The reaction solution was cooled to room temperature, diluted with EtOAc (20 mL) and washed with brine (30 mL). The organic phase was separated, dried over Na$_2$SO$_4$, and concentrated in vacuo. The residue was purified by preparative TLC (eluted with CH$_2$Cl$_2$/methanol=10:1) to afford the desired product (11.2 mg, 16%) as a white solid. m/z=357.2 [M+1]+; $^1$H NMR (400 MHz, CD$_3$OD): δ 7.98 (s, 1H), 7.78-7.98 (m, 2H), 7.59-7.63 (m, 3H), 7.741 (s, 1H), 7.30-7.36 (m, 4H), 7.22-7.24 (m, 1H), 3.80-3.84 (m, 2H), 3.76-3.77 (m, 1H), 3.53 (s, 2H), 3.33-3.37 (m, 2H).

The following compounds were prepared in a similar way:

3-Phenyl-6-[3-(pyrazin-2-yloxy)-azetidin-1-ylmethyl]-7H-imidazo[1,5-a]pyrazin-8-one

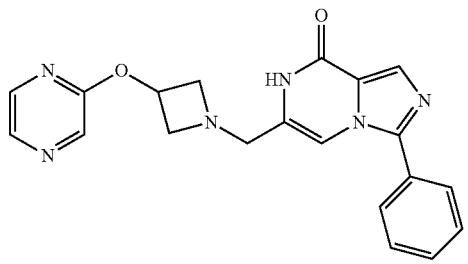 [SMILES: O=c1[nH]c(CN2CC(Oc3cnccn3)C2)cn2c(-c3ccccc3)ncc12]

10% yield. $^1$H NMR (400 MHz, CDCl$_3$): δ 8.61 (s, 1H), 8.26 (s, 1H), 8.17 (d, J=2.8 Hz, 1H), 8.08 (s, 1H), 8.05 (dd, J=2.8 Hz, 1.2 Hz, 1H), 7.73-7.75 (m, 2H), 7.50-7.59 (m, 3H), 7.13 (s, 1H), 5.25-5.31 (m, 1H), 3.88-3.92 (m, 2H), 3.49 (s, 2H), 3.25-3.28 (m, 2H).

6-[3-(4-Ethyl-phenyl)-azetidin-1-ylmethyl]-3-phenyl-7H-imidazo-[1,5-a]pyrazin-8-one

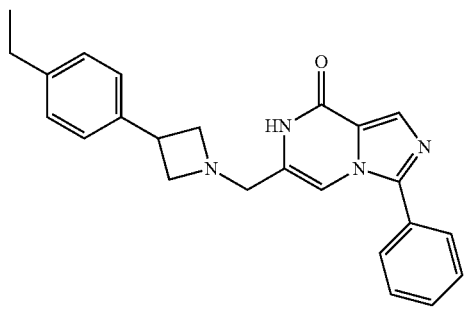 [SMILES: CCc1ccc(C2CN(Cc3cn4c(-c5ccccc5)ncc4c(=O)[nH]3)C2)cc1]

48% yield, m/z=385.2 [M+1]$^+$. $^1$H NMR (400 MHz, CDCl$_3$): δ 8.36 (s, 1H), 8.06 (s, 1H), 7.72-7.74 (m, 2H), 7.50-7.57 (m, 3H), 7.15-7.21 (m, 4H), 7.10 (s, 1H), 3.69-3.78 (m, 3H), 3.41 (s, 2H), 3.23-3.26 (m, 2H), 2.64 (q, J=7.2 Hz, 2H), 1.24 (t, J=7.2 Hz, 3H).

3-Phenyl-6-[3-(pyrimidin-2-yloxy)-azetidin-1-ylmethyl]-7H-imidazo[1,5-a]pyrazin-8-one

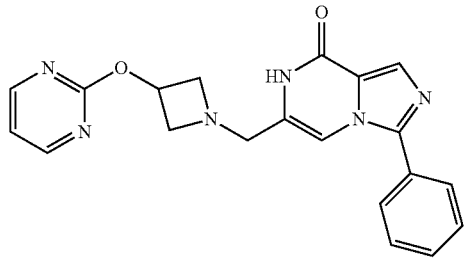 [SMILES: O=c1[nH]c(CN2CC(Oc3ncccn3)C2)cn2c(-c3ccccc3)ncc12]

12% yield. $^1$H NMR (400 MHz, CDCl$_3$): δ 8.51 (d, J=4.8 Hz, 2H), 8.51 (s, 1H), 8.08 (s, 1H), 7.73-7.75 (m, 2H), 7.52-7.58 (m, 3H), 7.12 (s, 1H), 6.98 (t, J=4.8 Hz, 1H), 5.30 (m, 1H), 3.94 (dd, J=6.4, 8.8 Hz, 2H), 3.48 (s, 2H), 3.29 (dd, J=6.0, 8.8 Hz, 2H).

6-[3-(6-Fluoro-pyridin-2-yloxy)-azetidin-1-ylmethyl]-3-phenyl-7H-imidazo[1,5-a]pyrazin-8-one

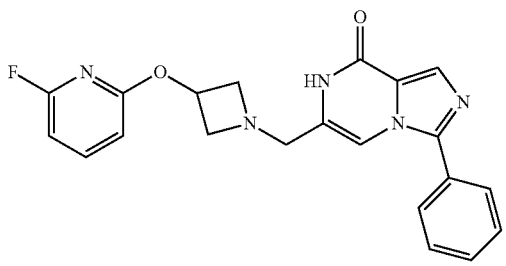 [SMILES: O=c1[nH]c(CN2CC(Oc3cccc(F)n3)C2)cn2c(-c3ccccc3)ncc12]

13% yield. $^1$H NMR (400 MHz, CD$_3$OD): δ 7.98 (s, 1H), 7.78-7.84 (m, 3H), 7.59-7.65 (m, 3H), 7.39 (s, 1H), 6.70 (d, J=8 Hz, 1H), 6.59 (dd, J=8.0, 2.0 Hz, 1H), 5.20-5.23 (m, 1H), 3.87-3.91 (m, 2H), 3.54 (s, 2H), 3.29-3.33 (m, 2H).

6-[3-(4,6-Dimethyl-pyrimidin-2-yloxy)-azetidin-1-ylmethyl]-3-phenyl-7H-imidazo[1,5-a]pyrazin-8-one

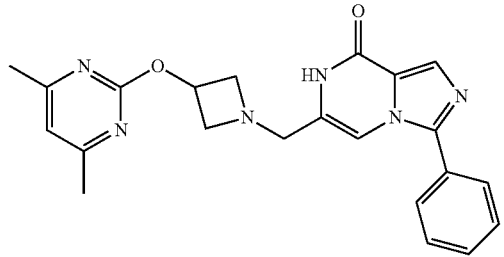 [SMILES: Cc1cc(C)nc(OC2CN(Cc3cn4c(-c5ccccc5)ncc4c(=O)[nH]3)C2)n1]

3% yield. $^1$H NMR (400 MHz, CDCl$_3$): δ 8.35 (s, 1H), 8.06 (s, 1H), 7.72-7.74 (m, 2H), 7.53-7.54 (m, 3H), 7.09 (s, 1H), 6.68 (s, 1H), 5.25-5.28 (m, 1H), 3.91 (m, 2H), 3.45 (s, 2H), 3.22 (m, 2H), 2.38 (s, 6H).

41

6-[3-(2-Fluoro-phenoxy)-azetidin-1-ylmethyl]-3-phenyl-7H-imidazo[1,5-a]pyrazin-8-one

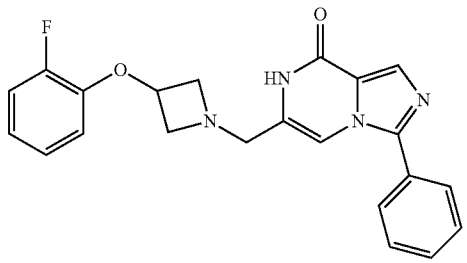 [SMILES: O=c1[nH]c(CN2CC(Oc3ccccc3F)C2)cn2c(-c3ccccc3)ncc12]

32% yield. ¹H NMR (400 MHz, CDCl₃): δ 8.39 (br s, 1H), 8.09 (s, 1H), 7.74-7.76 (m, 2H), 7.53-7.60 (m, 3H), 6.95-7.13 (m, 4H), 6.74-6.78 (m, 1H), 4.85-4.87 (m, 1H), 3.90-3.94 (m, 2H), 3.50 (s, 2H), 3.30-3.33 (m, 2H).

6-[3-(3-Fluoro-phenoxy)-azetidin-1-ylmethyl]-3-phenyl-7H-imidazo[1,5-a]pyrazin-8-one

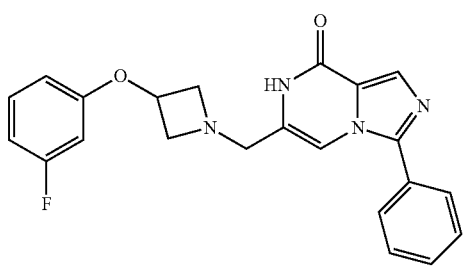 [SMILES: O=c1[nH]c(CN2CC(Oc3cccc(F)c3)C2)cn2c(-c3ccccc3)ncc12]

21% yield. ¹H NMR (400 MHz, CDCl₃): δ 8.36 (s, 1H), 8.06 (s, 1H), 7.71-7.73 (m, 2H), 7.50-7.56 (m, 3H), 7.10-7.26 (m, 1H), 7.10 (s, 1H), 6.67-6.68 (m, 1H), 6.51-6.54 (m, 1H), 6.45-6.48 (m, 1H), 4.77-4.80 (m, 1H), 3.85-3.89 (m, 2H), 3.46 (s, 2H), 3.21-3.25 (m, 2H).

6-[3-(4-Fluoro-phenoxy)-azetidin-1-ylmethyl]-3-phenyl-7H-imidazo[1,5-a]pyrazin-8-one

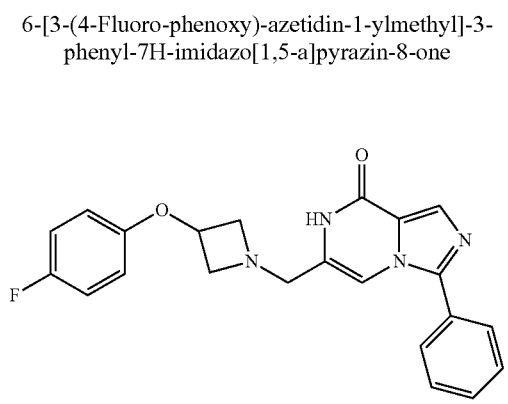

23% yield. ¹H NMR (400 MHz, CDCl₃): δ 8.22 (s, 1H), 8.08 (s, 1H), 7.71-7.73 (m, 2H), 7.50-7.56 (m, 3H), 7.09 (s, 1H), 6.94-6.99 (m, 2H), 6.67-6.70 (m, 2H), 4.73-4.76 (m, 1H), 3.83-3.87 (m, 2H), 3.43 (s, 2H), 3.19-3.23 (m, 2H).

42

6-(3-Methoxy-azetidin-1-ylmethyl)-3-phenyl-7H-imidazo[1,5-a]pyrazin-8-one

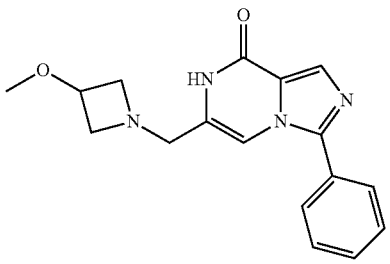 [SMILES: COC1CN(Cc2cn3c(-c4ccccc4)ncc3c(=O)[nH]2)C1]

25% yield. ¹H NMR (400 MHz, CDCl₃): δ 8.60 (s, 1H), 8.08 (s, 1H), 7.75-7.77 (d, J=1.6, 8.4 Hz, 2H), 7.53-7.59 (m, 3H), 7.12 (s, 1H), 4.08 (m, 1H), 3.67-3.70 (m, 2H), 3.43 (s, 2H), 3.28 (s, 3H), 3.02-3.06 (m, 2H).

3-Phenyl-6-[3-(quinoxalin-2-yloxy)-azetidin-1-ylmethyl]-7H-imidazo[1,5-a]pyrazin-8-one

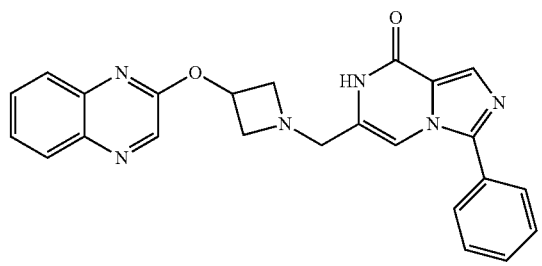 [SMILES: O=c1[nH]c(CN2CC(Oc3cnc4ccccc4n3)C2)cn2c(-c3ccccc3)ncc12]

22% yield. ¹H NMR (400 MHz, CDCl₃): δ 8.50 (s, 1H), 8.37 (s, 1H), 8.07 (s, 1H), 8.02 (d, J=8.0 Hz, 1H), 7.79 (d, J=8.0 Hz, 2H), 7.66-7.74 (m, 3H), 7.50-7.60 (m, 4H), 7.12 (s, 1H), 5.45 (m, 1H), 3.97-4.00 (dd, J=6.4, 8.0 Hz, 2H), 3.49 (s, 2H), 3.02-3.06 (dd, J=5.6, 8.0 Hz, 2H).

3-Phenyl-6-(3-phenylamino-pyrrolidin-1-ylmethyl)-7H-imidazo[1,5-a]pyrazin-8-one

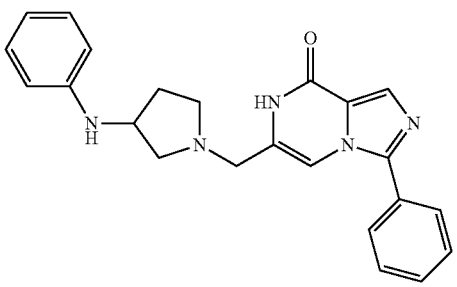 [SMILES: O=c1[nH]c(CN2CCC(Nc3ccccc3)C2)cn2c(-c3ccccc3)ncc12]

12% yield. ¹H NMR (400 MHz, CDCl₃): δ 8.41 (s, 1H), 8.07 (s, 1H), 7.73 (d, J=6.8 Hz, 2H), 7.52 (m, 3H), 7.17 (t, 2H), 7.10 (s, 1H), 6.72 (t, 1H), 6.58 (d, J=8.0 Hz, 2H), 4.02-4.10 (br s, 1H), 3.43 (m, 2H), 2.86 (m, 2H), 2.63 (m, 1H), 2.50 (m, 1H), 2.38 (m, 1H), 1.72 (m, 1H).

Example 2

6-[1-(3-Methoxy-azetidin-1-yl)-ethyl]-3-phenyl-7H-imidazo[1,5-a]pyrazin-8-one

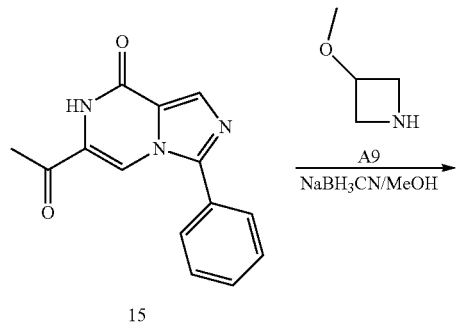

15

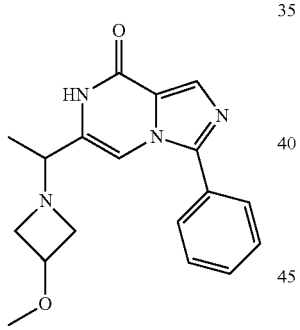

To a solution of compound 15 (200 mg, 0.79 mmol) and compound A9 (146 mg, 1.18 mmol) in methanol (5 mL) were added NaBH$_3$CN (497 mg, 7.9 mmol) in portions, followed by 3 drops of HOAc. The result mixture was stirred at 25° C. for 6 days. LC-MS showed that the starting material was almost consumed. The reaction mixture was quenched with water (40 mL), extracted with CH$_2$Cl$_2$ (30 mL×3). The combined organic phases were washed with brine (30 mL), dried over Na$_2$SO$_4$, filtered and concentrated in vacuo. The residue was purified by preparative TLC (eluted with CH$_2$Cl$_2$/MeOH=10:1) to afford the desired product (90 mg, 36%) as a white solid.

LC-MS: $t_R$=2.443 min, m/z=325.0 [M+1]$^+$.

$^1$H NMR (400 MHz, CDCl$_3$): δ 8.36 (s, 1H), 8.06 (s, 1H), 7.72-7.74 (m, 2H), 7.51-7.57 (m, 3H), 7.10 (s, 1H), 3.99-4.02 (m, 1H), 3.62-3.65 (m, 1H), 3.49-3.52 (m, 1H), 3.25 (s, 3H), 3.09-3.14 (m, 1H), 2.97-3.00 (m, 1H), 2.87-2.91 (m, 1H), 1.23-1.24 (d, J=6.4 Hz, 3H).

The following compounds were prepared in a similar way:

3-Phenyl-6-[1-(3-phenyl-azetidin-1-yl)-ethyl]-7H-imidazo[1,5-a]pyrazin-8-one

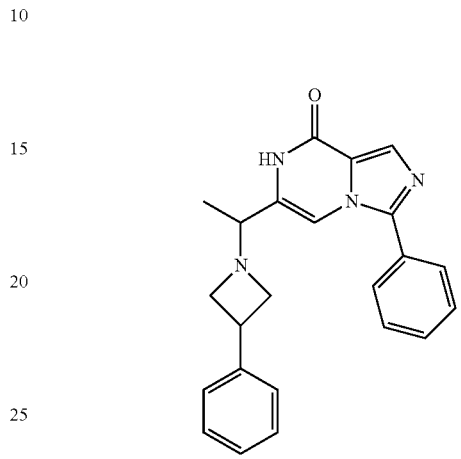

LC-MS: $t_R$=3.537 min, m/z=371.1 [M+1]$^+$.

12% yield. $^1$H NMR (400 MHz, CDCl$_3$): δ 8.31 (s, 1H), 8.07 (s, 1H), 7.73-7.75 (m, 2H), 7.49-7.57 (m, 3H), 7.33-7.35 (m, 2H), 7.27-7.31 (m, 2H), 7.22-7.23 (m, 1H), 7.12 (s, 1H), 3.74-3.77 (m, 1H), 3.64-3.69 (m, 2H), 3.20-3.24 (m, 1H), 3.14-3.17 (m, 2H), 1.25-1.27 (d, J=6.4 Hz, 3H).

6-{1-[3-(6-Fluoro-pyridin-2-yloxy)-azetidin-1-yl]-ethyl}-3-phenyl-7H-imidazo[1,5-a]pyrazin-8-one

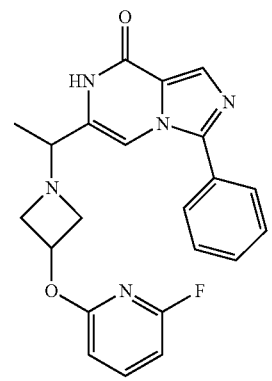 [SMILES: CC(c1cn2c(-c3ccccc3)ncc2c(=O)[nH]1)N1CC(Oc2cccc(F)n2)C1]

LC-MS: $t_R$=3.811 min, m/z=406.1 [M+1]$^+$.

15% yield. $^1$H NMR (400 MHz, CD$_3$OD): δ 7.85 (s, 1H), 7.66-7.22 (m, 3H), 7.47-7.53 (m, 3H), 7.27 (s, 1H), 6.57 (d, J=8.0 Hz, 1H), 6.47 (m, 1H), 5.06 (m, 1H). 3.78 (m, 1H), 3.66 (m, 1H), 3.10-3.15 (m, 3H), 1.22 (d, J=7.2 Hz, 3H).

6-{1-[3-(4-Fluoro-phenyl)-azetidin-1-yl]-ethyl}-3-phenyl-7H-imidazo[1,5-a]pyrazin-8-one

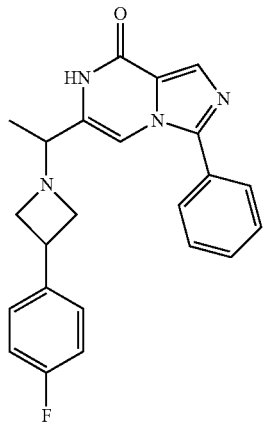 [SMILES: CC(c1cn2c(-c3ccccc3)ncc2c(=O)[nH]1)N1CC(c2ccc(F)cc2)C1]

LC-MS: $t_R$=3.980 min, m/z=389.0 [M+1]+.

19% yield. $^1$H NMR (400 MHz, CD$_3$OD): δ 7.84 (s, 1H), 7.66 (m, 2H), 7.49 (d, J=7.2 Hz, 3H), 7.24-7.30 (m, 3H), 6.90-6.94 (m, 2H), 3.69 (m, 1H), 3.54-3.62 (m, 2H). 3.26 (m, 1H), 3.16 (m, 2H), 1.20 (d, J=6.8 Hz, 3H).

6-{1-[3-(4-Ethyl-phenyl)-azetidin-1-yl]-ethyl}-3-phenyl-7H-imidazo[1,5-a]pyrazin-8-one

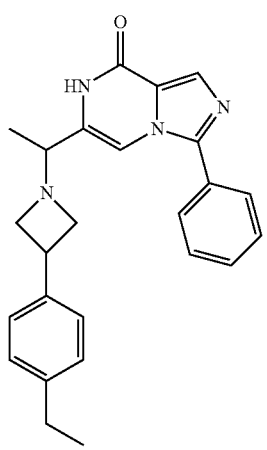 [SMILES: CCc1ccc(C2CN(C(C)c3cn4c(-c5ccccc5)ncc4c(=O)[nH]3)C2)cc1]

LC-MS: $t_R$=4.384 min, m/z=399.1 [M+1]$^+$.

39% yield. $^1$H NMR (400 MHz, CD$_3$OD): δ 7.86 (s, 1H), 7.68 (m, 2H), 7.51 (m, 3H), 7.31 (s, 1H), 7.14 (d, J=8.0 Hz, 2H), 7.04 (d, J=8.0 Hz, 2H), 3.69 (m, 1H), 3.52-3.60 (m, 2H), 3.12-3.18 (m, 3H), 2.51 (m, 2H), 1.21 (d, J=6.8 Hz, 3H), 1.11 (t, J=7.6 Hz, 3H).

3-Phenyl-6-{1-[3-(pyrimidin-2-yloxy)-azetidin-1-yl]-ethyl}-7H-imidazo[1,5-a]pyrazin-8-one

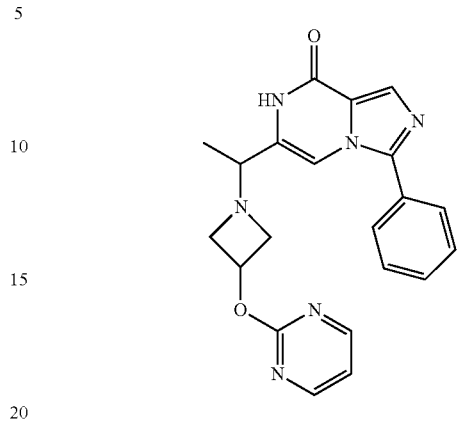

LC-MS: $t_R$=2.508 min, m/z=389.0 [M+1]$^+$.

18% yield. $^1$H NMR (400 MHz, CDCl$_3$): δ 10.65 (s, 1H), 8.58 (d, J=4.8 Hz, 2H), 7.85 (s, 1H), 7.77-7.79 (m, 2H), 7.53-7.60 (m, 3H), 7.32 (s, 1H), 7.14-7.16 (m, 1H). 5.11 (m, 1H), 3.75 (m, 1H), 3.63 (m, 1H), 3.29 (m, 1H), 3.11 (m, 2H), 1.22 (d, J=6.4 Hz, 3H).

6-{1-[3-(2-Fluoro-phenoxy)-azetidin-1-yl]-ethyl}-3-phenyl-7H-imidazo[1,5-a]pyrazin-8-one

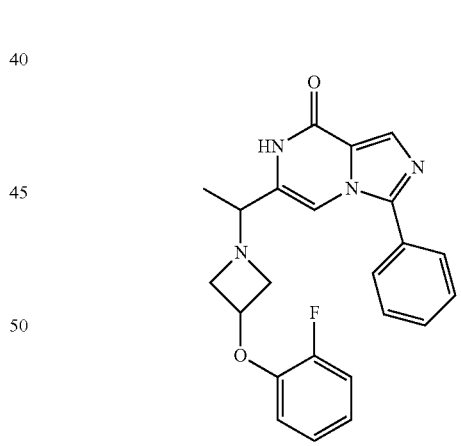

27% yield. $^1$H NMR (400 MHz, CDCl$_3$): δ 8.43-8.50 (m, 1H), 8.09 (s, 1H), 7.74-7.76 (m, 2H), 7.51-7.59 (m, 3H), 7.02-7.15 (m, 3H), 6.91-6.96 (m, 1H), 6.73-6.78 (m, 1H), 4.79-4.84 (m, 1H), 3.76-3.93 (m, 2H), 3.18-3.32 (m, 3H), 1.30-1.31 (d, J=6.8 Hz, 3H).

47

6-{1-[3-(4-Fluoro-phenoxy)-azetidin-1-yl]-ethyl}-3-phenyl-7H-imidazo[1,5-a]pyrazin-8-one

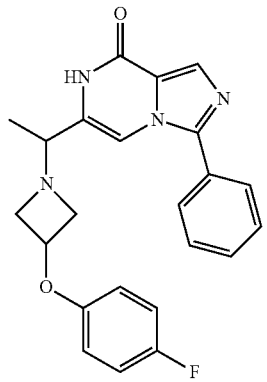 [SMILES: CC(c1cn2c(-c3ccccc3)ncc2c(=O)[nH]1)N1CC(Oc2ccc(F)cc2)C1]

30% yield. ¹H NMR (400 MHz, CDCl₃): δ 8.23 (s, 1H), 8.06 (s, 1H), 7.71-7.73 (m, 2H), 7.50-7.57 (m, 3H), 7.12 (s, 1H), 6.93-6.98 (m, 2H), 6.67-6.71 (m, 2H), 4.76-4.78 (m, 1H), 3.73-3.74 (m, 2H), 3.12-3.22 (m, 3H), 1.23-1.29 (m, 3H).

6-{1-[3-(3-Fluoro-phenoxy)-azetidin-1-yl]-ethyl}-3-phenyl-7H-imidazo[1,5-a]pyrazin-8-one

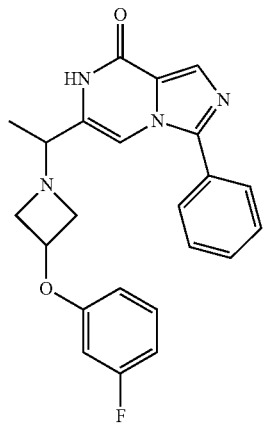 [SMILES: CC(c1cn2c(-c3ccccc3)ncc2c(=O)[nH]1)N1CC(Oc2cccc(F)c2)C1]

20% yield. ¹H NMR (400 MHz, CDCl₃): δ 8.23 (s, 1H), 8.08 (s, 1H), 7.71-7.73 (m, 2H), 7.51-7.56 (m, 3H), 7.10-7.26 (m, 1H), 7.11 (s, 1H), 6.65-6.70 (m, 1H), 6.45-6.54 (m, 1H), 6.45-6.49 (m, 1H), 4.73-4.76 (m, 1H), 3.72-3.88 (m, 2H), 3.11-3.24 (m, 3H), 1.25 (d, J=7.2 Hz, 3H).

48

6-[1-(3-Phenoxy-azetidin-1-yl)-ethyl]-3-phenyl-7H-imidazo[1,5-a]pyrazin-8-one

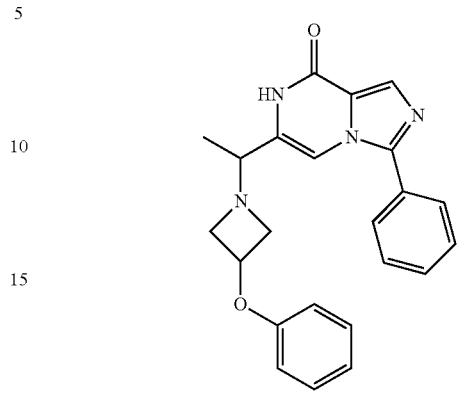

23% yield. ¹H NMR (400 MHz, CDCl₃): δ 8.23 (s, 1H), 8.06 (s, 1H), 7.70-7.73 (m, 2H), 7.53-7.54 (m, 3H), 7.24-7.26 (m, 2H), 7.09-7.11 (s, 1H), 6.97-6.98 (m, 1H), 6.73-6.76 (m, 2H), 4.76-4.78 (m, 1H), 3.72-3.87 (m, 2H), 3.11-3.22 (m, 3H), 1.21-1.28 (m, 3H).

1-Benzyl-4-(8-oxo-3-phenyl-7,8-dihydro-imidazo[1,5-a]pyrazin-6-yl)-pyrrolidine-3-carboxylic acid methyl ester

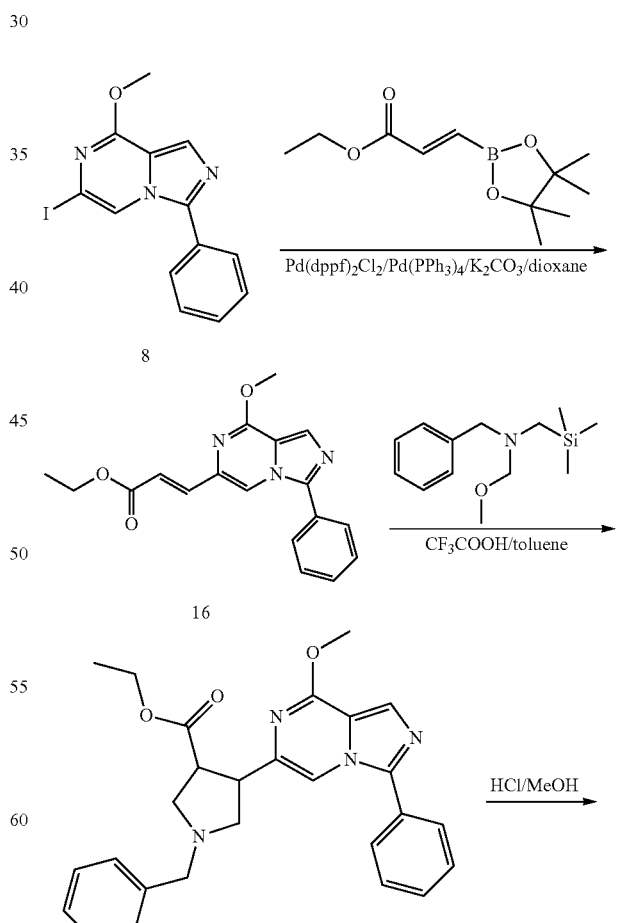

50

6-(1-Benzyl-4-methyl-pyrrolidin-3-yl)-3-phenyl-7H-imidazo[1,5-a]pyrazin-8-one

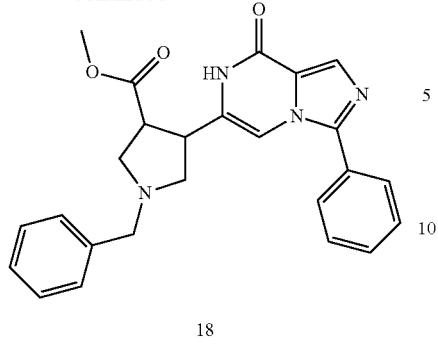

18

The mixture of 3-(4,4,5,5-tetramethyl-[1,3,2]dioxaborolan-2-yl)-acrylic acid ethyl ester (6.44 g, 28.5 mmol) (prepared according to the method described in Organic Letters, 2010, Vol. 12, No. 5, 1024-1027.), compound 8 (5 g, 14.2 mmol), $K_2CO_3$ (5.9 g, 42.7 mmol) and 1,4-dioxane (150 ml) were degassed by purging with $N_2$ three times, before tetrakis(triphenylphosphine)palladium(0) (165 mg, 0.14 mmol) and Pd(dppf)$_2$Cl$_{12}$ (521 mg, 0.71 mmol) were added. The reaction mixture was stirred at 75° C. for 48 hours under a $N_2$ atmosphere. The mixture was filtered, concentrated in vacuo. The residue was purified by column chromatography on silica gel (eluted with petroleum ether/EtOAc=20:1 to 5:1) to afford compound 16 (4.2 g, 91%). $^1$H NMR (400 MHz, CDCl$_3$): δ 7.87 (s, 1H), 7.82 (s, 1H), 7.76-7.78 (m, 2H), 7.50-7.58 (m, 3H), 7.42 (d, J=15.2 Hz, 1H), 6.90 (d, J=15.2 Hz, 1H), 4.24-4.29 (m, 2H), 4.15 (s, 3H), 1.32-1.36 (m, 3H).

To a solution of benzyl-methoxymethyl-trimethylsilanyl-methyl-amine (15.4 g, 65 mmol) in toluene (100 mL) was added compound 16 (4.2 g, 13 mmol), followed by dropwise addition of TFA (3.0 g, 26 mmol) under a nitrogen atmosphere. The mixture was stirred at 50° C. overnight. The reaction mixture was concentrated and purified by column chromatography on silica gel (eluted with CH$_2$Cl$_2$/methanol=200:1 to 20:1) to give compound 17 (5.1 g, 86%).

To a solution of compound 17 (20 mg, 0.044 mmol) in methanol (10 mL) was added 6N HCl (aq.) solution (5 mL). The resulting solution was stirred at 50° C. for 16 h. The reaction mixture was concentrated in vacuo to dryness. The saturated aqueous NaHCO$_3$ solution (20 mL) was added and the product was extracted with DCM (20 mL×3). The combined organic phases were dried over Na$_2$SO$_4$, filtered and concentrated in vacuum. The residue was purified by preparative TLC (eluted with CH$_2$Cl$_2$/methanol=15:1) to afford compound 18 (1.5 mg, 8%). $^1$H NMR (400 MHz, CDCl$_3$): δ 9.58-9.60 (m, 1H), 8.03 (s, 1H), 7.69-7.71 (m, 2H), 7.47-7.54 (m, 3H), 7.29-7.38 (m, 5H), 7.04 (s, 1H), 3.78-3.80 (m, 1H), 3.72 (s, 3H), 3.61-3.64 (m, 1H), 3.36-3.48 (m, 2H), 3.09-3.12 (m, 1H), 2.98-2.99 (m, 1H), 2.42-2.57 (m, 2H).

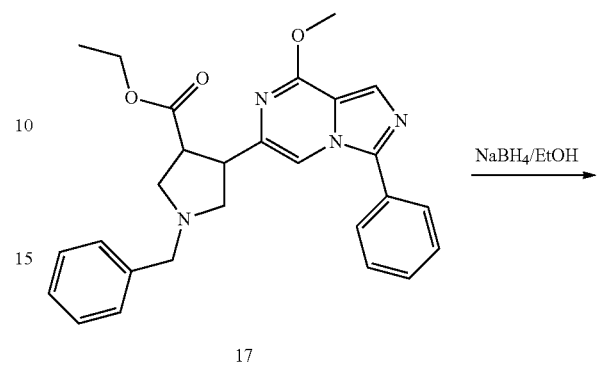

17

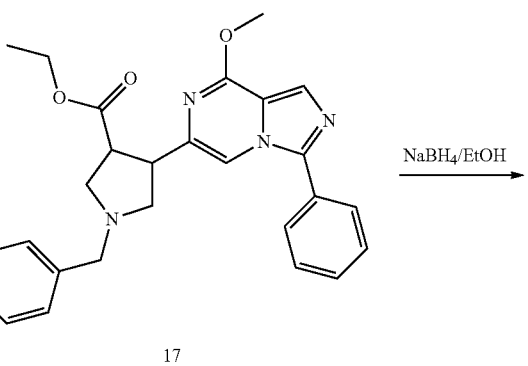

19

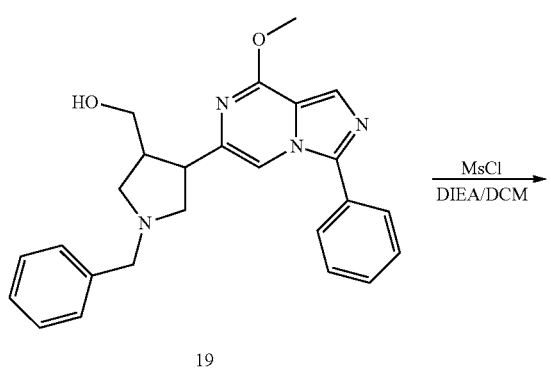

20

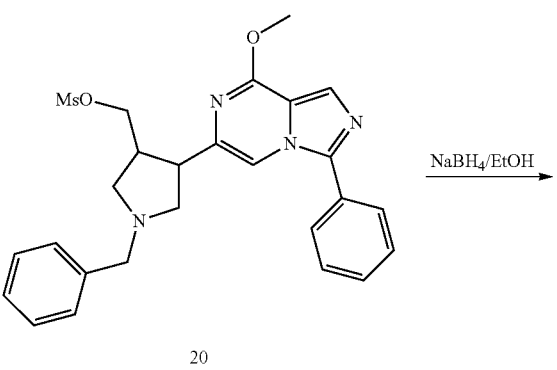

21

-continued

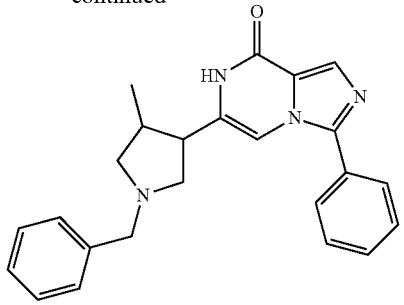

22

To a solution of compound 17 (1.8 g, 3.9 mmol) in EtOH (100 mL) was added NaBH$_4$ (0.73 g, 19.7 mmol) at 0° C. The reaction mixture was heated at reflux overnight. Water (200 ml) was added and the resulting mixture was extracted with DCM (100 mL×3). The combined organic phases were dried over Na$_2$SO$_4$, filtered and concentrated in vacuo. The residue was purified by column chromatography on silica gel (eluted with CH$_2$Cl$_2$/methanol=200:1 to 20:1) to afford compound 19 (0.91 g, 56%). $^1$H NMR (400 MHz, CDCl$_3$): δ 7.74-7.81 (m, 3H), 7.66 (s, 1H), 7.44-7.54 (m, 5H), 7.34-7.36 (m, 3H), 4.08 (s, 3H), 3.87-3.97 (m, 2H), 3.70-3.74 (m, 2H), 3.31-3.38 (m, 2H), 2.62-3.13 (m, 5H).

To a solution of compound 19 (100 mg, 0.24 mmol) and DIEA (94.2 mg, 0.72 mmol) in DCM (20 mL), was added MsCl (138 mg, 1.2 mmol) at 0° C. The reaction mixture was stirred at 25° C. overnight. The reaction mixture was diluted with DCM (50 mL) and washed with brine (30 mL). The organic phase was dried over Na$_2$SO$_4$, filtered and concentrated in vacuo. The residue was purified by column chromatography on silica gel (eluted with CH$_2$Cl$_2$/methanol=200:1 to 20:1) to afford compound 20 (55 mg, 46%). $^1$H NMR (400 MHz, CDCl$_3$): δ 7.68-7.73 (m, 3H), 7.61 (s, 1H), 7.39-7.49 (m, 3H), 7.19-7.33 (m, 5H), 4.21-4.27 (m, 2H), 4.01 (s, 3H), 3.71-.81 (m, 2H), 2.73-3.14 (m, 9H).

To a solution of compound 20 (230 mg, 0.47 mmol) in EtOH (20 ml), was added NaBH$_4$ (86 mg, 2.3 mmol) at 0° C. The reaction mixture was heated at reflux overnight. Water (50 ml) was added and the resulting mixture was extracted with DCM (50 mL×3). The combined organic phases were dried over Na$_2$SO$_4$, filtered and concentrated in vacuo. The residue was purified by column chromatography on silica gel (eluted with CH$_2$Cl$_2$/methanol=200:1 to 20:1) to afford compound 21 (120 mg, 64%).

To a solution of compound 21 (120 mg, 0.3 mmol) in methanol (30 mL), was added 6N HCl (aq.) solution (10 mL). The resulting solution was stirred at 50° C. for 16 h. The reaction solution was concentrated in vacuum to dryness. Saturated aqueous NaHCO$_3$ solution (20 mL) was added and the resulting mixture was extracted with DCM (30 mL×3). The combined organic phases were dried over Na$_2$SO$_4$, concentrated in vacuum. The residue was purified by preparative TLC (eluted with CH$_2$Cl$_2$/methanol=20:1) to afford compound 22 (30.4 mg, 26%). $^1$H NMR (400 MHz, CD$_3$OD): δ 7.98 (s, 1H), 7.78-7.79 (m, 2H), 7.38-7.76 (m, 9H), 4.32 (s, 2H), 3.41-3.65 (m, 3H), 2.91-3.06 (m, 2H), 2.60-2.63 (m, 1H), 1.16-1.18 (m, 3H).

In Vitro Testing
PDE9 Inhibition Assay

A PDE9 assay may for example, be performed as follows: The assay is performed in 60 uL samples containing a fixed amount of the relevant PDE enzyme (sufficient to convert 20-25% of the cyclic nucleotide substrate), a buffer (50 mM HEPES7.6; 10 mM MgCl$_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 uL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and IC$_{50}$ values can be calculated using the Xlfit extension to EXCEL.

In the context of the present invention the assay was performed in 60 uL assay buffer (50 mM HEPES pH 7.6; 10 mM MgCl$_2$; 0.02% Tween20) containing enough PDE9 to convert 20-25% of 10 nM $^3$H-cAMP and varying amounts of inhibitors. Following a 1 hour incubation the reactions were terminated by addition of 15 uL 8 mg/mL yttrium silicate SPA beads (Amersham). The beads were allowed to settle for one hr in the dark before the plates were counted in a Wallac 1450 Microbeta counter. IC$_{50}$ values were calculated by non linear regression using XLfit (IDBS).

Results of the experiments showed that the tested compounds of the invention inhibit the PDE9 enzyme with IC$_{50}$ values below 250 nM.

The invention claimed is:
1. A compound having the structure (I):

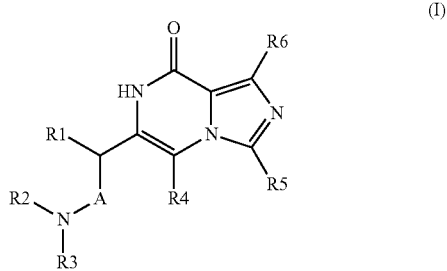

and a tautomer or a pharmaceutically acceptable acid addition salt thereof,
wherein:
A is absent or —CH$_2$—;
R1 is cyclized with R2 or R3 is cyclized with R2;
R1 is selected from the group consisting of —H and —CH$_2$R7,
wherein:
R7 is selected from the group consisting of —H, —CH$_3$, —CH$_2$CH$_3$, —CH$_2$CH$_2$CH$_3$ and —CH(CH$_3$)$_2$; or
R1, when cyclized with R2, is

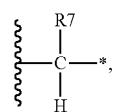

wherein:
R7 is selected from the group consisting of —H, —CH$_3$, —CH$_2$CH$_3$, —CH$_2$CH$_2$CH$_3$ and —CH(CH$_3$)$_2$; and

* is the cyclization point;
R2 is selected from the group consisting of:

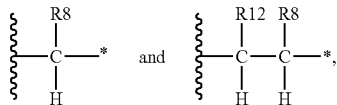

wherein:
R8 is selected from the group consisting of —H, —CH₃, —CH₂CH₃, —CH₂CH₂CH₃ and —CH(CH₃)₂;
R12 is selected from the group consisting of —H, —CH₃, —CH₂CH₃, —CH₂CH₂CH₃ and —CH(CH₃)₂; and
* is the cyclization point;
R3 is —CH(R10)(R11),
wherein:
R10 is selected from the group consisting of —H, —CH₃ and —CH₂CH₃; and
R11 is selected from the group consisting of optionally substituted C₆-C₁₀ aryl and optionally substituted C₃-C₉ heteroaryl;
wherein the substituents for C₆-C₁₀ aryl and C₃-C₉ heteroaryl are independently selected from the group consisting of —F, —Cl, —CN, —CF₃, —OCF₃, —OCH₃, —CH₃, —CH₂CH₃, —CH(CH₃)₂, —N(CH₃)₂ and cyclopropyl; or
R3, when cyclized with R2, is

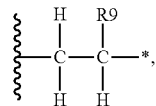

wherein:
R9 is selected from the group consisting of —H, —C₁-C₆ alkyl, C₃-C₆ cycloalkyl, C₆-C₁₀ aryl, substituted phenyl, optionally substituted C₃-C₉ heteroaryl, C₁-C₆ alkoxy, C₃-C₆ cycloalkoxy, optionally substituted C₆-C₁₀ aryloxy and optionally substituted C₃-C₉ heteroaryloxy; and
* is the cyclization point;
wherein the substituents for phenyl, C₃-C₉ heteroaryl, C₆-C₁₀ aryloxy and C₃-C₉ heteroaryloxy are independently selected from the group consisting of —F, —Cl, —CN, —CF₃, —OCF₃, —OCH₃, —CH₃, —CH₂CH₃, —CH(CH₃)₂, —N(CH₃)₂ and cyclopropyl;
R4 is selected from the group consisting of —H, —F, —Cl, —CN, —CF₃, —CH₃, —CH₂CH₃, —CH₂CH₂CH₃ and —CH(CH₃)₂;
R5 is selected from the group consisting of optionally substituted C₆-C₁₀ aryl, optionally substituted C₃-C₉ heteroaryl, optionally substituted C₃-C₆ heterocyclyl and optionally substituted C₃-C₆ cycloalkyl;
wherein the substituents for C₆-C₁₀ aryl, C₃-C₉ heteroaryl, C₃-C₆ heterocyclyl and C₃-C₆ cycloalkyl are independently selected from the group consisting of —F, —Cl, —CN, —CF₃, —OCF₃, —OCH₃, —CH₃, —CH₂CH₃, —CH(CH₃)₂, —N(CH₃)₂ and cyclopropyl; and R6 is selected from the group consisting of —H, —F, —Cl, —CN, —CF₃, —CH₃, —CH₂CH₃, —CH₂CH₂CH₃ and —CH(CH₃)₂.

2. The compound of claim 1, wherein R9 is selected from the group consisting of branched C₃-C₆ alkyl and branched C₃-C₆ alkoxy.

3. The compound of claim 1, wherein the C₃-C₉ heteroaryl of R5, the C₃-C₉ heteroaryl of R9 and the C₃-C₉ heteroaryl of R11 each independently comprise one or two nitrogen atoms.

4. The compound of claim 1, wherein the compound is selected from the group consisting of:
(1) 3-(4-fluorophenyl)-6-[1-(3-methoxyazetidin-1-yl)ethyl]-7H-imidazo[1,5-a]pyrazin-8-one,
(2) 6-[1-(cyclohexylmethylamino)ethyl]-3-phenyl-7H-imidazo[1,5-a]pyrazin-8-one,
(3) 6-[(3-methoxyazetidin-1-yl)methyl]-3-phenyl-7H-imidazo[1,5-a]pyrazin-8-one,
(4) 3-phenyl-6-[(3-pyrazin-2-yloxyazetidin-1-yl)methyl]-7H-imidazo[1,5-a]pyrazin-8-one,
(5) 3-phenyl-6-[(3-pyrimidin-2-yloxyazetidin-1-yl)methyl]-7H-imidazo[1,5-a]pyrazin-8-one,
(6) 6-[[3-[(6-fluoro-2-pyridyl)oxy]azetidin-1-yl]methyl]-3-phenyl-7H-imidazo[1,5-a]pyrazin-8-one,
(7) 3-phenyl-6-[1-(3-pyrimidin-2-yloxyazetidin-1-yl)ethyl]-7H-imidazo[1,5-a]pyrazin-8-one,
(8) 3-phenyl-6-[(3-phenylazetidin-1-yl)methyl]-7H-imidazo[1,5-a]pyrazin-8-one,
(9) 6-[[benzyl(methyl)amino]methyl]-3-phenyl-7H-imidazo[1,5-a]pyrazin-8-one,
(10) methyl 1-benzyl-4-(8-oxo-3-phenyl-7H-imidazo[1,5-a]pyrazin-6-yl)pyrrolidine-3-carboxylate,
(11) 6-[[3-(4-ethylphenyl)azetidin-1-yl]methyl]-3-phenyl-7H-imidazo[1,5-a]pyrazin-8-one,
(12) 6-[1-[3-(4-fluorophenyl)azetidin-1-yl]propyl]-3-phenyl-7H-imidazo[1,5-a]pyrazin-8-one,
(13) 3-phenyl-6-[(3-quinoxalin-2-yloxyazetidin-1-yl)methyl]-7H-imidazo[1,5-a]pyrazin-8-one,
(14) 6-[[3-(4,6-dimethylpyrimidin-2-yl)oxyazetidin-1-yl]methyl]-3-phenyl-7H-imidazo[1,5-a]pyrazin-8-one,
(15) 3-phenyl-6-[1-(3-pyrazin-2-yloxyazetidin-1-yl)ethyl]-7H-imidazo[1,5-a]pyrazin-8-one,
(16) 6-[[3-(3-fluorophenoxy)azetidin-1-yl]methyl]-3-phenyl-7H-imidazo[1,5-a]pyrazin-8-one,
(17) 6-[(3-anilinopyrrolidin-1-yl)methyl]-3-phenyl-7H-imidazo[1,5-a]pyrazin-8-one,
(18) 3-phenyl-6-[1-(3-phenylazetidin-1-yl)ethyl]-7H-imidazo[1,5-a]pyrazin-8-one,
(19) 6-[[3-(4-fluorophenyl)azetidin-1-yl]methyl]-3-phenyl-7H-imidazo[1,5-a]pyrazin-8-one,
(20) 6-[1-(3-methoxyazetidin-1-yl)ethyl]-3-phenyl-7H-imidazo[1,5-a]pyrazin-8-one,
(21) 6-[(3-phenoxyazetidin-1-yl)methyl]-3-phenyl-7H-imidazo[1,5-a]pyrazin-8-one,
(22) 6-[(3-methoxyazetidin-1-yl)-phenyl-methyl]-3-phenyl-7H-imidazo[1,5-a]pyrazin-8-one,
(23) 6-[[3-(4-fluorophenoxy)azetidin-1-yl]methyl]-3-phenyl-7H-imidazo[1,5-a]pyrazin-8-one,
(24) 6-[1-[3-(3-fluorophenoxy)azetidin-1-yl]ethyl]-3-phenyl-7H-imidazo[1,5-a]pyrazin-8-one,
(25) 6-[1-(3-phenoxyazetidin-1-yl)ethyl]-3-phenyl-7H-imidazo[1,5-a]pyrazin-8-one,
(26) 6-[1-[3-(4-fluorophenoxy)azetidin-1-yl]ethyl]-3-phenyl-7H-imidazo[1,5-a]pyrazin-8-one,
(27) 6-[1-[3-[(6-fluoro-2-pyridyl)oxy]azetidin-1-yl]ethyl]-3-phenyl-7H-imidazo[1,5-a]pyrazin-8-one,

(28) 6-[1-[3-(4-fluorophenyl)azetidin-1-yl]ethyl]-3-phenyl-7H-imidazo[1,5-a]pyrazin-8-one,
(29) 6-[1-[3-(4-methyl-2-pyridyl)azetidin-1-yl]ethyl]-3-phenyl-7H-imidazo[1,5-a]pyrazin-8-one,
(30) 6-[1-[3-(4-ethylphenyl)azetidin-1-yl]ethyl]-3-phenyl-7H-imidazo[1,5-a]pyrazin-8-one,
(31) 6-(1-benzyl-4-methyl-pyrrolidin-3-yl)-3-phenyl-7H-imidazo[1,5-a]pyrazin-8-one,
(32) 6-[1-[3-(2-fluorophenoxy)azetidin-1-yl]ethyl]-3-phenyl-7H-imidazo[1,5-a]pyrazin-8-one,
(33) 6-[[3-(2-fluorophenoxy)azetidin-1-yl]methyl]-3-phenyl-7H-imidazo[1,5-a]pyrazin-8-one,
(34) 6-[1-[3-(4-methoxyphenyl)azetidin-1-yl]ethyl]-3-phenyl-7H-imidazo[1,5-a]pyrazin-8-one,
(35) 4-[1-[(8-oxo-3-phenyl-7H-imidazo[1,5-a]pyrazin-6-yl)methyl]azetidin-3-yl]benzonitrile,
(36) 3-phenyl-6-[1-(3-pyrimidin-2-ylazetidin-1-yl)ethyl]-7H-imidazo[1,5-a]pyrazin-8-one,
(37) 3-phenyl-6-[[3-(2-pyridyl)azetidin-1-yl]methyl]-7H-imidazo[1,5-a]pyrazin-8-one,
(38) 4-[1-[1-(8-oxo-3-phenyl-7h-imidazo[1,5-a]pyrazin-6-yl)ethyl]azetidin-3-yl]benzonitrile,
(39) 3-cyclopentyl-6-[(3-pyrimidin-2-yloxyazetidin-1-yl)methyl]-7H-imidazo[1,5-a]pyrazin-8-one,
(40) 3-cyclopentyl-6-[1-[3-(4-fluorophenyl)azetidin-1-yl]ethyl]-7H-imidazo[1,5-a]pyrazin-8-one,
(41) 3-cyclopentyl-6-[[3-(4-methoxyphenyl)azetidin-1-yl]methyl]-7H-imidazo[1,5-a]pyrazin-8-one,
(42) 3-cyclopentyl-6-[1-(3-pyrimidin-2-yloxyazetidin-1-yl)ethyl]-7H-imidazo[1,5-a]pyrazin-8-one,
(43) 6-[4-methyl-1-(2-pyridylmethyl)pyrrolidin-3-yl]-3-phenyl-7H-imidazo[1,5-a]pyrazin-8-one,
(44) 6-[[3-(4-fluorophenyl) azetidin-1-yl]methyl]-3-tetrahydropyran-4-yl-7H-imidazo[1,5-a]pyrazin-8-one,
(45) 6-[(3-benzyloxyazetidin-1-yl)methyl]-3-(4-fluorophenyl)-7H-imidazo[1,5-a]pyrazin-8-one,
(46) 3-cyclopentyl-6-[[3-(3-methylquinoxalin-2-yloxyazetidin-1-yl]methyl]-7H-imidazo[1,5-a]pyrazin-8-one,
(47) 3-cyclopentyl-6-[1-[3-(4-fluorophenoxy)azetidin-1-yl]ethyl]-7H-imidazo[1,5-a]pyrazin-8-one,
(48) 3-cyclopentyl-6-[[3-(4-dimethylaminophenyl) azetidin-1-yl]methyl]-7H-imidazo[1,5-a]pyrazin-8-one,
(49) 6-[[3-(2-fluorophenoxy)azetidin-1-yl]methyl]-3-(4-fluorophenyl)-7H-imidazo[1,5-a]pyrazin-8-one,
(50) 6-[[3-(2-fluorophenoxy)azetidin-1-yl]methyl]-3-tetrahydropyran-4-yl-7H-imidazo[1,5-a]pyrazin-8-one,
(51) 6-[[3-(4-dimethylaminophenyl)azetidin-1-yl]methyl]-3-(4-fluorophenyl)-7H-imidazo[1,5-a]pyrazin-8-one,
(52) 3-cyclopentyl-6-[1-[3-(2-fluorophenoxy)azetidin-1-yl]ethyl]-7H-imidazo[1,5-a]pyrazin-8-one,
(53) 3-(4-fluorophenyl)-6-[(3-pyrimidin-2-ylazetidin-1-yl)methyl]-7H-imidazo[1,5-a]pyrazin-8-one,
(54) 6-[(3-pyrimidin-2-ylazetidin-1-yl)methyl]-3-tetrahydropyran-4-yl-7H-imidazo[1,5-a]pyrazin-8-one,
(55) 3-(4-fluorophenyl)-6-[(3-pyrazin-2-yloxyazetidin-1-yl)methyl]-7H-imidazo[1,5-a]pyrazin-8-one,
(56) 6-[(3-benzyloxyazetidin-1-yl)methyl]-3-cyclopentyl-7H-imidazo[1,5-a]pyrazin-8-one,
(57) 3-cyclopentyl-6-[(3-isopropoxyazetidin-1-yl)methyl]-7H-imidazo[1,5-a]pyrazin-8-one,
(58) 3-cyclopentyl-6-[(3-isobutoxyazetidin-1-yl)methyl]-7H-imidazo[1,5-a]pyrazin-8-one,
(59) 3-cyclopentyl-6-[1-[3-(4-dimethylaminophenyl)azetidin-1-yl]ethyl]-7H-imidazo[1,5-a]pyrazin-8-one,
(60) 3-(4-fluorophenyl)-6-[[3-(6-fluoro-2-pyridyl)oxy]azetidin-1-yl]methyl]-7H-imidazo[1,5-a]pyrazin-8-one,
(61) 3-(4-fluorophenyl)-6-[[3-(2-pyridyl)azetidin-1-yl]methyl]-7H-imidazo[1,5-a]pyrazin-8-one,
(62) 6-[[3-(2-pyridyl)azetidin-1-yl]methyl]-3-tetrahydropyran-4-yl-7H-imidazo[1,5-a]pyrazin-8-one,
(63) 6-[[3-(4-fluorophenoxy)azetidin-1-yl]methyl]-3-(4-fluorophenyl)-7H-imidazo[1,5-a]pyrazin-8-one,
(64) 3-tetrahydropyran-4-yl-6-[[3-[4-(trifluoromethoxy)phenoxy]azetidin-1-yl]methyl]-7H-imidazo[1,5-a]pyrazin-8-one,
(65) 6-[[3-[(6-fluoro-2-pyridyl)oxy]azetidin-1-yl]methyl]-3-tetrahydropyran-4-yl-7H-imidazo[1,5-a]pyrazin-8-one,
(66) 6-[(3-anilinopyrrolidin-1-yl)methyl]-3-tetrahydropyran-4-yl-7H-imidazo[1,5-a]pyrazin-8-one,
(67) 6-[(3-benzyloxyazetidin-1-yl)methyl]-3-tetrahydropyran-4-yl-7H-imidazo[1,5-a]pyrazin-8-one,
(68) 6-[(3-phenylazetidin-1-yl)methyl]-3-tetrahydropyran-4-yl-7H-imidazo[1,5-a]pyrazin-8-one,
(69) 6-[[3-(4-methoxyphenyl)azetidin-1-yl]methyl]-3-tetrahydropyran-4-yl-7H-imidazo[1,5-a]pyrazin-8-one,
(70) 3-tetrahydropyran-4-yl-6-[[3-[5-(trifluoromethyl)-2-pyridyl]azetidin-1-yl]methyl]-7H-imidazo[1,5-a]pyrazin-8-one,
(71) 6-[[3-(3-fluorophenoxy)azetidin-1-yl]methyl]-3-tetrahydropyran-4-yl-7H-imidazo[1,5-a]pyrazin-8-one,
(72) 6-[(3-quinoxalin-2-yloxyazetidin-1-yl)methyl]-3-tetrahydropyran-4-yl-7H-imidazo[1,5-a]pyrazin-8-one,
(73) 3-(4-fluorophenyl)-6-[(3-phenoxyazetidin-1-yl)methyl]-7H-imidazo[1,5-a]pyrazin-8-one,
(74) 3-(4-fluorophenyl)-6-[[3-[4-(trifluoromethoxy)phenoxy]azetidin-1-yl]methyl]-7H-imidazo[1,5-a]pyrazin-8-one,
(75) 6-[[3-(4-fluorophenoxy)azetidin-1-yl]methyl]-3-tetrahydropyran-4-yl-7H-imidazo[1,5-a]pyrazin-8-one,
(76) 3-(4-fluorophenyl)-6-[[3-(4-fluorophenyl) azetidin-1-yl]methyl]-7H-imidazo[1,5-a]pyrazin-8-one,
(77) 3-(4-fluorophenyl)-6-[[3-[5-(trifluoromethyl)-2-pyridyl]azetidin-1-yl]methyl]-7H-imidazo[1,5-a]pyrazin-8-one,
(78) 6-[[3-(4-ethylphenyl) azetidin-1-yl]methyl]-3-tetrahydropyran-4-yl-7H-imidazo[1,5-a]pyrazin-8-one,
(79) 6-[4-methyl-1-[[6-(trifluoromethyl)-3-pyridyl]methyl]pyrrolidin-3-yl]-3-tetrahydropyran-4-yl-7H-imidazo[1,5-a]pyrazin-8-one,
(80) 4-[1-[(8-oxo-3-tetrahydropyran-4-yl-7H-imidazo[1,5-a]pyrazin-6-yl)methyl]azetidin-3-yl]oxybenzonitrile,
(81) 6-[4-methyl-1-(2-pyridylmethyl)pyrrolidin-3-yl]-3-tetrahydropyran-4-yl-7H-imidazo[1,5-a]pyrazin-8-one,
(82) 6-[[3-(4-pyridyloxy)azetidin-1-yl]methyl]-3-tetrahydropyran-4-yl-7H-imidazo[1,5-a]pyrazin-8-one,
(83) 6-[[3-(3-pyridyloxy)azetidin-1-yl]methyl]-3-tetrahydropyran-4-yl-7H-imidazo[1,5-a]pyrazin-8-one,
(84) 6-[(3-pyrimidin-2-yloxypyrrolidin-1-yl)methyl]-3-tetrahydropyran-4-yl-7H-imidazo[1,5-a]pyrazin-8-one,
(85) 3-(4-fluorophenyl)-6-[(3-phenoxypyrrolidin-1-yl)methyl]-7H-imidazo[1,5-a]pyrazin-8-one,
(86) 3-(4-fluorophenyl)-6-[(3-pyrimidin-2-yloxypyrrolidin-1-yl)methyl]-7H-imidazo[1,5-a]pyrazin-8-one,
(87) 3-(4-fluorophenyl)-6-[[3-(4-pyridyloxy)azetidin-1-yl]methyl]-7H-imidazo[1,5-a]pyrazin-8-one,
(88) 3-(4-fluorophenyl)-6-[[3-(3-pyridyloxy)azetidin-1-yl]methyl]-7H-imidazo[1,5-a]pyrazin-8-one,

(89) 6-[1-[(4-fluorophenyl)methyl]-4-methyl-pyrrolidin-3-yl]-3-tetrahydropyran-4-yl-7H-imidazo[1,5-a]pyrazin-8-one,
(90) 6-[4-methyl-1-(pyrimidin-2-ylmethyl)pyrrolidin-3-yl]-3-tetrahydropyran-4-yl-7H-imidazo[1,5-a]pyrazin-8-one,
(91) 6-[1-(3-pyrimidin-2-ylazetidin-1-yl)ethyl]-3-tetrahydropyran-4-yl-7H-imidazo[1,5-a]pyrazin-8-one,
(92) 4-[1-[[3-(4-fluorophenyl)-8-oxo-7H-imidazo[1,5-a]pyrazin-6-yl]methyl]azetidin-3-yl]oxybenzonitrile,
(93) 3-[1-[[3-(4-fluorophenyl)-8-oxo-7H-imidazo[1,5-a]pyrazin-6-yl]methyl]azetidin-3-yl]oxybenzonitrile,
(94) 3-[1-[(8-oxo-3-tetrahydropyran-4-yl-7H-imidazo[1,5-a]pyrazin-6-yl)methyl]azetidin-3-yl]oxybenzonitrile,
(95) 3-(4-fluorophenyl)-6-[[3-[3-(trifluoromethyl)phenoxy]azetidin-1-yl]methyl]-7H-imidazo[1,5-a]pyrazin-8-one,
(96) 4-[1-[[3-(4-fluorophenyl)-8-oxo-7H-imidazo[1,5-a]pyrazin-6-yl]methyl]azetidin-3-yl]benzonitrile,
(97) 6-[4-methyl-1-(quinoxalin-6-ylmethyl)pyrrolidin-3-yl]-3-tetrahydropyran-4-yl-7H-imidazo[1,5-a]pyrazin-8-one,
(98) 4-[[3-methyl-4-(8-oxo-3-tetrahydropyran-4-yl-7H-imidazo[1,5-a]pyrazin-6-yl)pyrrolidin-1-yl]methyl]benzonitrile,
(99) 3-(4-fluorophenyl)-6-[1-[(4-fluorophenyl)methyl]-4-methyl-pyrrolidin-3-yl]-7H-imidazo[1,5-a]pyrazin-8-one,
(100) 1-bromo-3-(4-fluorophenyl)-6-[1-[(4-fluorophenyl)methyl]-4-methyl-pyrrolidin-3-yl]-7H-imidazo[1,5-a]pyrazin-8-one,
(101) 6-[1-[(6-methoxy-3-pyridyl)methyl]-4-methyl-pyrrolidin-3-yl]-3-tetrahydropyran-4-yl-7H-imidazo[1,5-a]pyrazin-8-one,
(102) 6-[4-methyl-1-[(5-methylpyrazin-2-yl)methyl]pyrrolidin-3-yl]-3-tetrahydropyran-4-yl-7H-imidazo[1,5-a]pyrazin-8-one,
(103) 6-[[3-[(4-fluorophenyl)methoxy]azetidin-1-yl]methyl]-3-tetrahydropyran-4-yl-7H-imidazo[1,5-a]pyrazin-8-one,
(104) 3-tetrahydropyran-4-yl-6-[[3-[4-(trifluoromethyl)phenoxy]azetidin-1-yl]methyl]-7H-imidazo[1,5-a]pyrazin-8-one,
(105) 3-cyclopentyl-1,5-difluoro-6-[(3-phenylazetidin-1-yl)methyl]-7H-imidazo[1,5-a]pyrazin-8-one,
(106) 4-[1-[(8-oxo-3-tetrahydropyran-4-yl-7H-imidazo[1,5-a]pyrazin-6-yl)methyl]azetidin-3-yl]benzonitrile,
(107) 3-[1-[(8-oxo-3-tetrahydropyran-4-yl-7H-imidazo[1,5-a]pyrazin-6-yl)methyl]azetidin-3-yl]benzonitrile,
(108) 6-[[3-[(4-chlorophenyl)methoxy]azetidin-1-yl]methyl]-3-(4-fluorophenyl)-7H-imidazo[1,5-a]pyrazin-8-one,
(109) 3-(4-fluorophenyl)-6-[[3-[4-(trifluoromethyl)phenoxy]azetidin-1-yl]methyl]-7H-imidazo[1,5-a]pyrazin-8-one,
(110) 3-(4-chlorophenyl)-6-[1-[(4-fluorophenyl)methyl]-4-methyl-pyrrolidin-3-yl]-7H-imidazo[1,5-a]pyrazin-8-one,
(111) 1-bromo-3-(4-chlorophenyl)-6-[1-[(4-fluorophenyl)methyl]-4-methyl-pyrrolidin-3-yl]-7H-imidazo[1,5-a]pyrazin-8-one,
(112) 6-[1-(3-methoxyazetidin-1-yl)ethyl]-6-methyl-3-tetrahydropyran-4-yl-7H-imidazo[1,5-a]pyrazin-8-one,
(113) 3-(4-fluorophenyl)-6-[[3-(p-tolylmethoxy)azetidin-1-yl]methyl]-7H-imidazo[1,5-a]pyrazin-8-one,
(114) 3-(4-fluorophenyl)-6-[4-methyl-1-(2-pyridylmethyl)pyrrolidin-3-yl]-7H-imidazo[1,5-a]pyrazin-8-one,
(115) 6-[1-(cyclohexylmethyl)-4-methyl-pyrrolidin-3-yl]-3-tetrahydropyran-4-yl-7H-imidazo[1,5-a]pyrazin-8-one,
(116) 3-(4-fluorophenyl)-6-[1-(3-isopropoxyazetidin-1-yl)ethyl]-7H-imidazo[1,5-a]pyrazin-8-one,
(117) 6-[1-(3-isopropoxyazetidin-1-yl)ethyl]-3-tetrahydropyran-4-yl-7H-imidazo[1,5-a]pyrazin-8-one,
(118) 6-[[3-(4-chlorophenoxy)azetidin-1-yl]methyl]-3-(4-fluorophenyl)-7H-imidazo[1,5-a]pyrazin-8-one,
(119) 6-[1-[(4-fluorophenyl)methyl]-4-methyl-pyrrolidin-3-yl]-3-[4-(trifluoromethoxy)phenyl]-7H-imidazo[1,5-a]pyrazin-8-one,
(120) 3-(4-fluorophenyl)-6-[1-[3-[4-(trifluoromethoxy)phenoxy]azetidin-1-yl]ethyl]-7H-imidazo[1,5-a]pyrazin-8-one,
(121) 6-[[3-(2,6-difluorophenoxy)azetidin-1-yl]methyl]-3-(4-fluorophenyl)-7H-imidazo[1,5-a]pyrazin-8-one,
(122) 3-(3,5-difluorophenyl)-6-[[3-(4-methoxyphenyl)azetidin-1-yl]methyl]-7H-imidazo[1,5-a]pyrazin-8-one,
(123) 3-(4-fluorophenyl)-6-[[3-(4-methoxyphenyl)azetidin-1-yl]methyl]-7H-imidazo[1,5-a]pyrazin-8-one,
(124) 3-(4-fluorophenyl)-6-[1-[3-(4-fluorophenyl)azetidin-1-yl]ethyl]-7H-imidazo[1,5-a]pyrazin-8-one,
(125) 3-tetrahydrofuran-3-yl-6-[[3-[3-(trifluoromethyl)phenyl]pyrrolidin-1-yl]methyl]-7H-imidazo[1,5-a]pyrazin-8-one,
(126) 3-(4-fluorophenyl)-6-[1-[3-(4-methoxyphenyl)azetidin-1-yl]ethyl]-7H-imidazo[1,5-a]pyrazin-8-one,
(127) 3-(4,4-difluorocyclohexyl)-6-[[3-(4-methoxyphenyl)azetidin-1-yl]methyl]-7H-imidazo[1,5-a]pyrazin-8-one,
(128) 3-(4,4-difluorocyclohexyl)-6-[(3-methoxyazetidin-1-yl)methyl]-7H-imidazo[1,5-a]pyrazin-8-one, and
(129) 6-[[3-(4-fluorophenoxy)azetidin-1-yl]methyl]-3-tetrahydrofuran-3-yl-7H-imidazo[1,5-a]pyrazin-8-one or a tautomer or a pharmaceutically acceptable acid addition salt thereof.

5. A pharmaceutical composition comprising a therapeutically effective amount of the compound of claim 1, and one or more pharmaceutically acceptable carriers, diluents and excipients.

6. A method of inhibiting phosphodiesterase 9 activity in a subject, comprising administering a therapeutically effective amount of a compound of claim 1.

7. The method of claim 6, wherein the subject has a neurodegenerative disorder selected from the group consisting of Alzheimer's disease, mental retardation, cognitive impairment associated with schizophrenia, attention-deficit/hyperactivity disorder, age-related cognitive decline, and substance-induced psychotic disorder.

8. The method of claim 7, wherein the substance-induced psychotic disorder is psychosis induced by alcohol, psychosis induced by amphetamine, psychosis induced by *cannabis*, psychosis induced by cocaine, psychosis induced by hallucinogens, psychosis induced by inhalants, psychosis induced by opioids or psychosis induced by phencyclidine.

9. A compound, wherein the compound is 6-[4-methyl-1-(pyrimidin-2-ylmethyl)pyrrolidin-3-yl]-3-tetrahydropyran-4-yl-7H-imidazo[1,5-a]pyrazin-8-one, and a tautomer or a pharmaceutically acceptable acid addition salt thereof.

10. A pharmaceutical composition comprising a therapeutically effective amount of the compound of claim 9, and one or more pharmaceutically acceptable carriers, diluents and excipients.

* * * * *